(12) United States Patent
Lebrilla et al.

(10) Patent No.: US 7,651,847 B2
(45) Date of Patent: Jan. 26, 2010

(54) METHODS OF OLIGOSACCHARIDE PROFILING FOR THE DETECTION OF CANCER

(75) Inventors: Carlito B. Lebrilla, Davis, CA (US); Hyun Joo An, Davis, CA (US); Kit S. Lam, Davis, CA (US); Suzanne Miyamoto, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 226 days.

(21) Appl. No.: 11/157,478

(22) Filed: Jun. 20, 2005

(65) Prior Publication Data

US 2006/0035304 A1    Feb. 16, 2006

Related U.S. Application Data

(60) Provisional application No. 60/582,250, filed on Jun. 22, 2004.

(51) Int. Cl.
*C12Q 1/34* (2006.01)
*C12Q 1/02* (2006.01)
*C12N 5/00* (2006.01)
*C12N 5/02* (2006.01)
*C12N 5/08* (2006.01)
*C12N 5/16* (2006.01)
*C12N 5/22* (2006.01)

(52) U.S. Cl. .................. 435/29; 435/325; 435/372; 435/392; 607/901

(58) Field of Classification Search ............... 435/18, 435/29, 325, 372, 392; 607/901
See application file for complete search history.

(56) References Cited

U.S. PATENT DOCUMENTS 6,680,203 B2    1/2004    Dasseux et al.

FOREIGN PATENT DOCUMENTS

| WO | WO 03/016464 A2 | 2/2003 |
| WO | WO 03/016464 A3 | 2/2003 |
| WO | WO 2005/111627 A2 | 11/2005 |
| WO | WO 2005/111627 A3 | 11/2005 |

OTHER PUBLICATIONS

Cancilla et al 1998. Alkaline Degradation of Oligosaccharides with Matrix-Assisted Laser Desorption/ Fourier Transform Mass Spectrometry: for Sequencing Oligosaccharides, Analytical Chemistry, vol. 70, 663-672.*
Jacobs et al. "The CA 125 tumour-associated antigen: a review of the literature", Human Reproduction, 4 (1): 1-12, (1989).
Johnson et al. "P.J, Glycan Composition of Serum Alpha-fetoprotein in Patients with Hepatocellular Carncinoma and Non-seminomatous Germ Cell Tumuor". British Journal of Cancer, 81(7): 1188-1195, (1999).
Kim et al. "Osteopontin as a potential diagnostic biomarker for ovarian cancer" JAMA (13) 287:1671-1679, (2002).
Lloyd et al. Comparison of O-linked Carbohydrate Chains in MUC-1 Mucin from Normal Breast Epithelial Cell Lines and Breast Carninoma Cell Lines, Journal of Biological Chemistry 271(52):33325-33334, (1996).
Masahashi et al. "Serum CA 125 levels in patients with endometriosis: changes in CA 125 levels during menstruation" Obstetrics and Gynecology 72(3 Pt 1): 328-31, (1988).
Peracaula et al. Altered Glycosylation Pattern Allows the Distinction Between Prostrate-specific Antigen (PSA) from Normal and Tumor Origins. Glycobiology, 12(8):457-470 Abstract p. 468, col. 2, lines 50-58, (2003).
Stimplf et al. "Expression of mucins and cytokeratins in ovarian cancer cell lines" Cancer Letters 145:133-141, (1999).
Van Den Steen et al. "Oligosaccharides of recombinant mouse gelatinase B variants" Crit. Rev. Biochem. Mol. Biol 33:151-208, (1998).
An, H.J. et al., "Profiling of Glycans in Serum for the Discovery of Potential Biomarkers for Ovarian Cancer," *Journal of Proteome Research*, 2006, vol. 5, No. 7, pp. 1626-1635.
Supplementary Partial European Search report mailed on Oct. 19, 2007, for EP Application No. 05789016.2, four pages.
Wong, N.K. et al., "Characterization of the Oilgosaccharides Associated With the Human Ovarian Tumor Marker CA125," *Journal of Biological Chemistry*, Aug. 1, 2003, vol. 278, No. 31, pp. 28619-28634.
Bast et al. "Reactivity of a Monoclonal Antibody with Human Ovarian Carcinoma" J Clin. Invest. 68:1331-1337, (Nov. 1981).
Bast et al. "A Radioimmunoassay Using a Monoclonal antibody to Monitor the course of Epithelial Ovarian Cancer" New England Journal Medicine, 309 (15): 883-887, (1983).
Croce et al. "Tissue and serum MUC1 mucin detection in breast cancer patients" Breast Cancer Research Treatment, vol. 81:195-207, (2003).
Gillan et al. "Periostin secreted by epithelial ovarian carcinoma is a ligand for $\alpha_v\beta_3$ and $\alpha_v\beta_5$ integrins and promotes cell motility," Cancer Res. 62: 5358-5364, (2002).
Hanisch et al. "MUC1 glycoforms in breast cancer: cell line T47D as a model for carcinoma-associated alterations of O-glycosylation" Eur. J. Biochem. 236:318-327, (1996).
Hanisch "O-glycosylation of the mucin type" Biol. Chem. 382:143-149, (2001).
Hellström et al. "The HE4 (WFDC2) Protein is a Biomarker for Ovarian Carcinoma" Cancer Res., 63:3695-3700, (2003).
Hollingsworth et al. "Mucins in Cancer: Protection and control of the cell surface" Nature Reviews, Cancer, 4:45-60, (Jan. 2004).

* cited by examiner (Continued)

*Primary Examiner*—Jon P Weber
*Assistant Examiner*—Kailash C Srivastava
(74) *Attorney, Agent, or Firm*—Townsend and Townsend and Crew LLP

(57) ABSTRACT

The present invention provides methods for identifying oligosaccharides specific to cancer and methods for determining a strain of cancer in an individual. The present invention also provides methods for diagnosing cancer or a stage of cancer in an individual by detecting the presence or absence of specific cancer markers and methods for treating cancer by administering antibodies directed to such markers. In addition, the present invention provides cancer markers comprising O-linked oligosaccharides and kits for diagnosing or treating cancer.

26 Claims, 20 Drawing Sheets

| | | | |
|---|---|---|---|
| Core 1 | Galβ1-3GalNAc- | Core 2 | GlcNAc<br>\| β1-6<br>Galβ1-3GalNAc- |
| Core 3 | GlcNAcβ1-3GalNAc- | Core 4 | GlcNAc<br>\| β1-6<br>GlcNAcβ1-3GalNAc- |
| Core 5 | GalNAcα1-3GalNAc- | Core 6 | GlcNAcβ1-6GalNAc- |
| Core 7 | GalNAcα1-6GalNAc- | Core 8 | Galα1-3GalNAc- |

N-acetylneuraminic acid (NeuAc)

(2)

N-glycolylneuraminic acid (NeuGc)

$[M-H+2Na]^+ = 510$ $[M-H+2Na]^+ = 1006$ $[M-H+2Na]^+ = 1119$ $[M-H+2Na]^+ = 1168$ $[M-H+2Na]^+=559$ $[M-H+2Na]^+= 721$ $[M-H+2Na]^+= 867$ $[M-H+2Na]^+= 925$ $[M-H+2Na]^+ = 883$ $[M-H+2Na]^+ = 899$ $[M-H+2Na]^+ = 925$ $[M-H+2Na]^+ = 981$ $[M+Na]^+ = 756$ $[M+Na]^+ = 855$ $[M+Na]^+ = 1262$

METHODS OF OLIGOSACCHARIDE PROFILING FOR THE DETECTION OF CANCER

CROSS-REFERENCES TO RELATED APPLICATIONS

The present application claims priority to U.S. Provisional Application No. 60/582,250, filed Jun. 22, 2004, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant (or Contract) No. RO1-GM049077, awarded by the National Institute of Health. The Government has certain rights in this invention.

BACKGROUND OF THE INVENTION

Ovarian cancer is the fifth leading cause of death from cancer and has the highest mortality rate among the gynecologic malignancies in the United States. According to the American Cancer Society (2002), approximately 23,300 women will be diagnosed with ovarian cancer in the United States and 13,900 will die from the disease. Ovarian tumors are classified by the World Health Organization (WHO) according to their cell type and include, for example, epithelial, germ cell, stromal, and metastatic tumors. Epithelial tumors are the most common type with abnormal masses that typically develop on the surface of ovaries. Stromal and germ cell tumors are typically rare.

Ovarian cancer is often called a "silent killer" due to the lack of noticeable early symptoms. In fact, symptoms specific to ovarian cancer develop only after the disease has spread out of the ovary. Early diagnosis is important because ovarian cancer is very treatable when detected early. For example, if ovarian cancer is detected before it has spread out of the ovary, 95% of women will survive longer than five years; however, if diagnosed in advance stages, only 28% of women will survive longer than five years.

Current approaches to identifying biological markers for diagnosing and treating cancers have mainly focused on proteomics. For example, proteins such as osteopontin, periostin, and HE7 (WFDC2) were identified through proteomics or gene expression analyses and have been suggested to be potential diagnostic markers for ovarian cancer (Kim et al., *JAMA*, 287:1671-1679 (2002); Hellstrom et al., *Cancer Res.*, 63:3695-3700 (2003); Gillan et al., *Cancer Res.*, 62:5358-5364 (2002)). However, their utility as markers for diagnosing cancer is unknown.

Mucins are expressed and secreted by various epithelial cell types (Van den Steen et al., *Crit. Rev. Biochem. Mol. Biol.*, 33:151-208 (1998)). Epithelial cells are expressed on the outer walls of tissues/organs and are involved in cell-cell or cell-matrix interactions, often acting as the interface between tissues and their environment. Mucins are secreted by normal secretory epithelial cells and have a central role in maintaining homeostasis and the survival of cells (Hanisch, *Biol. Chem.*, 382:143-149 (2001)). Mucins are often characterized as large glycoproteins associated with high levels of glycosylation. Oligosaccharides, primarily O-linked or mucin-type oligosaccharides, make up a large fraction of the mass of mucins (Van den Steen et al., id).

Mucins have long been implicated in the pathogenesis of cancer (Hollingsworth et al., *Nat. Rev. Cancer,* 4:45-60 (2004)). Most types of adenocarcinomas (i.e., epithelial cell cancers) are often accompanied by high levels of mucin production (Hollingsworth et al., id). For example, mucins such as MUC1 and CA 125 (MUC 16) are elevated in ovarian cancer (Stimpfl et al., *Cancer Lett.,* 145:133-141 (1999)). MUC 1 is found to be commonly associated with breast cancer (Hanisch et al., *Eur. J. Biochem.*, 236:318-327 (1996); Lloyd et al., *J. Biol. Chem.*, 271:33325-33334 (1996); Croce et al., *Br. Cancer Res. Treatment,* 81:195-207 (2003)). CA 125 (MUC 16) has been commonly used in the clinic as an ovarian cancer marker and has been assessed as a useful biochemical tool for both monitoring and prognostic evaluation of patients with ovarian cancer (Bast et al., *N. Engl. J Med.,* 309:883-887 (1983); Bast et al., *J. Clin. Invest.,* 68:1331-1337 (1981)). However, elevated serum CA 125 levels are found in only 50% of those patients with FIGO (International Federation of Gynecology and Obstetrics scoring system) stage I ovarian cancer (Jacobs et al., *Hum. Reprod.,* 4:1-12 (1989)). In addition, a significant proportion of women with benign conditions such as endometriosis or pelvic inflammatory disease also have raised CA 125 levels (Jacobs et al., id; Mashasi et al., *Obstret. Gynecol.,* 72:328-331 (1988)). Therefore, elevated serum CA 125 levels is not an adequate indicator for detecting early onset ovarian cancer.

The evaluation of the levels of mucins such as CA 125 are complicated by several factors. First, mucins are highly heterogeneous glycoproteins with high molecular weights (e.g., $10^7$ Daltons). Second, antibody methods currently used to detect mucins are imprecise and not quantitative. Third, mucins that are commonly detected, such as CA 125, are not expressed equally by the different tumor types of ovarian cancer.

As such, there is a need in the art for the identification of biological markers for the early detection or diagnosis of adenocarcinomas such as ovarian cancer or breast cancer. The present invention satisfies this and other needs.

BRIEF SUMMARY OF THE INVENTION

The present invention provides methods for identifying oligosaccharides specific to cancer (i.e., cancer markers) and methods for determining a strain of cancer in an individual. The present invention also provides methods for diagnosing cancer or a stage of cancer in an individual by detecting the presence or absence of specific cancer markers and methods for treating cancer by administering antibodies directed to such markers. In addition, the present invention provides cancer markers comprising O-linked oligosaccharides and kits for diagnosing or treating cancer.

As such, in one aspect, the present invention provides a method for identifying an oligosaccharide specific to cancer, the method comprising:

(a) selectively releasing the oligosaccharides from a test sample, wherein the test sample is a sample from a cancer cell line or an individual having cancer;

(b) obtaining a mass spectrum of the oligosaccharides from the test sample using matrix-assisted laser desorption ionization (MALDI)-Fourier transform mass spectrometry (FTMS); and (c) comparing the mass spectrum from the test sample to the mass spectrum from a control sample, wherein the oligosaccharide specific to cancer is identified by the presence of a unique oligosaccharide in the mass spectrum from the test sample.

In another aspect, the present invention provides a method for determining a strain of cancer in an individual, the method comprising:
  (a) obtaining a mass spectrum of the oligosaccharides from a sample from the individual using MALDI-FTMS, wherein the oligosaccharides have been selectively released from the sample; and
  (b) comparing the mass spectrum from the sample to a mass spectrum profile from at least one known strain of cancer, wherein the strain of cancer is determined by a similarity between the mass spectrum from the sample and the mass spectrum profile from one of the known strains of cancer.

In yet another aspect, the present invention provides a method for diagnosing cancer in an individual, the method comprising:
  detecting the presence or absence of a unique oligosaccharide in a sample from the individual, wherein the presence of the unique oligosaccharide indicates that the individual has cancer.

In still yet another aspect, the present invention provides a method for diagnosing cancer in an individual, the method comprising:
  (a) obtaining a mass spectrum of the oligosaccharides from a sample from the individual using MALDI-FTMS, wherein the oligosaccharides have been selectively released from the sample; and
  (b) comparing the mass spectrum from the sample to the mass spectrum from a control sample, wherein a higher ratio of NeuGc-containing O-linked oligosaccharides to NeuAc-containing O-linked oligosaccharides in the sample relative to the control sample indicates that the individual has cancer.

In a further aspect, the present invention provides a method for diagnosing cancer in an individual, the method comprising:
  (a) obtaining a mass spectrum of the oligosaccharides from a sample from the individual using MALDI-FTMS, wherein the oligosaccharides have been selectively released from the sample; and
  (b) comparing the mass spectrum from the sample to the mass spectrum from a control sample, wherein a lower percentage of sulfated O-linked oligosaccharides in the sample relative to the control sample indicates that the individual has cancer.

In another aspect, the present invention provides a method for diagnosing cancer in an individual, the method comprising:
  (a) obtaining a mass spectrum of the oligosaccharides from a sample from the individual, wherein the oligosaccharides have been selectively released from the sample; and
  (b) determining the presence or absence of a cancer marker selected from the group consisting of a sulfated oligosaccharide, an N-acetylneuraminic acid (NeuAc)-containing oligosaccharide, an N-glycolylneuraminic acid (NeuGc)-containing oligosaccharide, a neutral oligosaccharide, a hexose (Hex)-containing oligosaccharide, a hexuronic acid (HexA)-containing oligosaccharide, and combinations thereof in the mass spectrum, wherein the presence of the cancer marker indicates that the individual has cancer.

In yet another aspect, the present invention provides a method for diagnosing a stage of cancer in an individual, the method comprising:

(a) obtaining a mass spectrum of the oligosaccharides from a sample from the individual, wherein the oligosaccharides have been selectively released from the sample;
  (b) determining the presence or absence of a first cancer marker in the mass spectrum, wherein the first cancer marker is selected from the group consisting of 1 HexNAc:1 Hex:1 NeuAc; 2 HexNAc:1 NeuAc:1 Fuc; 1 HexNAc:3 Hex:1 NeuAc; 1 HexNAc:2 Hex:1 NeuGc; 3 HexNAc:1 NeuGc; 1 HexNAc:2 Hex:1 NeuGc:1 Fuc; 1 HexNAc:3 Hex:1 Fuc:1 $SO_3H$; 2 HexNAc:1 Hex:2 Fuc:1 $SO_3H$; 2 HexNAc:3 Hex:1 $SO_3H$; 4 HexNAc:1 Hex: 1 $SO_3H$; 5 HexNAc:1 Hex:1 Fuc:1 $SO_3H$; 2 HexNAc:2 Fuc; 2 HexNAc:1 Hex:1 Fuc; 4 HexNAc; 4 HexNAc:1 Hex; 1 HexNAc:3 Hex:2 Fuc; 1 HexNAc:4 Hex:1 Fuc; 3 HexNAc:1 Hex:2 Fuc; 2 HexNAc:4 Hex:1 Fuc; and combinations thereof; and
  (c) determining the presence or absence of a second cancer marker in the mass spectrum, wherein the second cancer marker is selected from the group consisting of 1 HexNAc:2 Hex:1 NeuAc; 2 HexNAc:1 Hex:1 NeuAc; 3 HexNAc:1 Hex:1 NeuAc:3 Fuc; 1 HexNAc:1 Hex:1 NeuGc:1 Fuc; 2 HexNAc:1 NeuGc:1 Fuc; 3 HexNAc:4 Hex:1 NeuGc; 1 HexNAc:1 Hex:1 $SO_3H$; 2 HexNAc:2 Hex:2 Fuc:1 $SO_3H$; 1 HexNAc:2 Fuc; 1 HexNAc:2 Hex:2 Fuc; 6 HexNAc; 3 HexNAc:3 Hex:2 Fuc; 4 HexNAc:3 Hex: 1 Fuc; and combinations thereof, wherein the presence of the first cancer marker and the absence of the second cancer marker indicates that the individual has an early stage cancer and wherein the presence of the second cancer marker indicates that the individual has a late stage cancer.

In still yet another aspect, the present invention provides a cancer marker comprising an O-linked oligosaccharide having a composition selected from the group consisting of 1 HexNAc:1 Hex:1 $SO_3H$; 1 HexNAc:3 Hex:1 Fuc:1 $SO_3H$; 2 HexNAc:1 Hex:2 Fuc:1 $SO_3H$; 2 HexNAc:3 Hex:1 $SO_3H$; 4 HexNAc:1 Hex:1 $SO_3H$; 2 HexNAc:2 Hex:2 Fuc:1 $SO_3H$; 5 HexNAc:1 Hex:1 Fuc:1 $SO_3H$; 1 HexNAc:1 Hex:1 NeuAc; 1 HexNAc:2 Hex:1 NeuAc; 2 HexNAc:1 NeuAc:1 Fuc; 2 HexNAc:1 Hex:1 NeuAc; 1 HexNAc:3 Hex:1 NeuAc; 3 HexNAc:1 Hex:1 NeuAc:3 Fuc; 1 HexNAc:1 Hex:1 NeuGc:1 Fuc; 1 HexNAc:2 Hex:1 NeuGc; 2 HexNAc:1 NeuGc:1 Fuc; 3 HexNAc:1 NeuGc; 1 HexNAc:2 Hex:1 NeuGc:1 Fuc; 3 HexNAc:4 Hex:1 NeuGc; 1 HexNAc:2 Fuc; 2 HexNAc:2 Fuc; 2 HexNAc:1 Hex:1 Fuc; 4 HexNAc; 1 HexNAc:2 Hex:2 Fuc; 4 HexNAc:1 Hex; 1 HexNAc:3 Hex:2 Fuc; 1 HexNAc:4 Hex:1 Fuc; 3 HexNAc:1 Hex:2 Fuc; 2 HexNAc:4 Hex:1 Fuc; 6 HexNAc; 3 HexNAc:3 Hex:2 Fuc; 4 HexNAc:3 Hex:1 Fuc; 2 Hex; 1 HexNAc:1 Hex; 3 Hex; 1 HexNAc:2 Hex; 3 Hex:1 HexNAc; 1 Hex*:2 Hex:1 HexNAc; 4 Hex:1 HexNAc; 3 Hex:2 HexNAc; 1 Hex*:2 Hex:2 HexNAc; 4 Hex:2 HexNAc; 1 Hex*:3 Hex:2 HexNAc; 5 Hex:2 HexNAc; 4 Hex:3 HexNAc; 5 Hex:3 HexNAc; 1 Hex*:4 Hex:3 HexNAc; 2 Hex*:3 Hex:1 HexNAc; m/z 221+$[HexA]_1$; m/z 221+$[HexA]_2$; m/z 221+$[HexA]_3$; m/z 221+$[HexA]_4$; m/z 221+$[HexA]_5$; m/z 221+$[HexA]_6$; m/z 221+$[HexA]_7$; m/z 361+$[HexA]_1$; m/z 361+$[HexA]_2$; m/z 361+$[HexA]_3$; m/z 361+$[HexA]_4$; m/z 361+$[HexA]_5$; m/z 361+$[HexA]_6$; m/z 551+$[HexA]_1$; m/z 551+$[HexA]_2$; m/z 551+$[HexA]_3$; m/z 551+$[HexA]_4$; m/z 551+$[HexA]_5$; m/z 555+$[HexA]_1$; m/z 555+$[HexA]_2$; m/z 555+$[HexA]_3$; m/z 604+$[HexA]_1$; m/z 604+$[HexA]_2$; m/z 604+$[HexA]_3$; m/z 604+$[HexA]_4$; and combinations thereof.

In a further aspect, the present invention provides a method for treating cancer in an individual in need thereof, the method comprising:

administering to the individual a therapeutically effective amount of an antibody that binds specifically to a cancer marker.

In another aspect, the present invention provides a kit for diagnosing cancer in an individual, the kit comprising:
(a) an array comprising a plurality of cancer markers;
(b) a plurality of antibodies that binds specifically to the plurality of cancer markers on the array; and
(c) directions for use of the array and the plurality of antibodies with a sample from the individual.

In yet another aspect, the present invention provides a kit for treating cancer in an individual in need thereof, the kit comprising:
(a) an antibody that binds specifically to a cancer marker; and
(b) directions for use of the antibody.

Other objects, features, and advantages of the present invention will be apparent to one of skill in the art from the following detailed description and figures.

BRIEF DESCRIPTION OF THE DRAWINGS

FIG. 1 shows the known core structures found in O-linked oligosaccharides.

DETAILED DESCRIPTION OF THE INVENTION

I. Abbreviations

Figure 2:
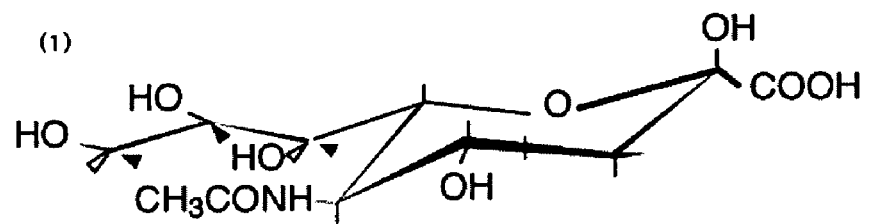
FIG. 2 shows the structures of N-acetylneuraminic acid (NeuAc) and N-glycolylneuraminic acid (NeuGc).
Figure 2:
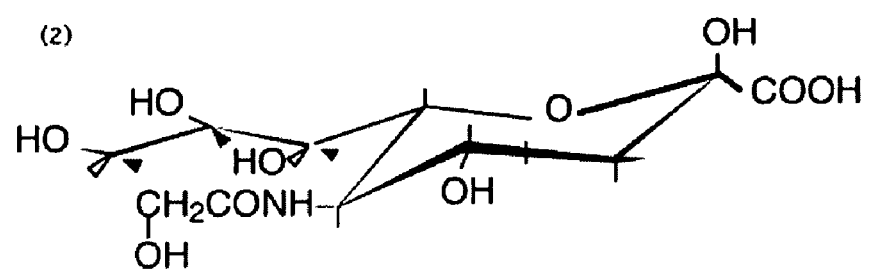

MALDI, matrix-assisted laser desorption ionization; FTMS, Fourier transform mass spectrometry; IRMPD, infrared multiphoton dissociation; Hex, hexose; Hex*, acetyl hexose; HexA, hexuronic acid; HexNAc, N-acetylhexosamine; NeuAc, N-acetylneuraminic acid; NeuGc, N-glycolylneuraminic acid; Fuc, fucose; $SO_3H$, sulfate.

II. Definitions

As used herein, the following terms have the meanings ascribed to them unless specified otherwise.

The term "cancer" refers to any of various malignant neoplasms characterized by the proliferation of anaplastic cells that tend to invade surrounding tissue and metastasize to new body sites. Examples of different types of cancer include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers; and osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia. The term "adenocarcinoma" refers to any of various malignant neoplasms originating in glandular epithelium and includes, without limitation, ovarian cancer and breast cancer.

The term "sample" refers to any biological specimen obtained from an individual. Suitable samples for use in the present invention include, without limitation, whole blood, plasma, serum, saliva, urine, stool, tears, and any other bodily fluid or tissue. In a preferred embodiment, the sample is a serum sample. The term also encompasses any specimen obtained from a cell line including, without limitation, conditioned medium and a cellular extract such as a membrane extract, a cytosolic extract, a nuclear extract, etc. One skilled in the art understands that samples such as serum and conditioned medium can be diluted prior to analysis.

The term "marker" refers to any molecule that is detectable in a biological sample and indicative of a disease, disorder, or a susceptibility to a disease or disorder. Preferably, the marker is a glycan or sugar molecule (e.g., a monosaccharide, oligosaccharide, or polysaccharide). In preferred embodiments of the present invention, the marker is a unique oligosaccharide species that is specific to a particular type of cancer. As a non-limiting example, the unique oligosaccharide species can be an O-linked oligosaccharide, an N-linked oligosaccharide, a free oligosaccharide, or combinations thereof.

The term "cancer marker" refers to a marker that is indicative of cancer in an individual. The term encompasses a molecule that is produced by or present on a cancer cell or a normal cell, but whose level is modulated in a test sample from a cancer cell line or an individual having cancer compared to its level in a control sample from a normal cell line or an individual not having cancer. More particularly, the term includes, without limitation: (1) a molecule that is specifically expressed by or present on a cancer cell but not expressed by or present on a normal cell; (2) a molecule whose expression is enhanced in a cancer cell compared to a normal cell; (3) a molecule that is specifically expressed by or present on a normal cell but not expressed by or present on a cancer cell; and (4) a molecule whose expression is reduced in a cancer cell compared to a normal cell. In preferred embodiments of the present invention, the cancer marker is an O-linked oligosaccharide. For example, the O-linked oligosaccharide can be a sulfated oligosaccharide, a NeuAc-containing oligosaccharide, a NeuGc-containing oligosaccharide, a HexA-containing oligosaccharide, a Hex-containing oligosaccharide, a neutral oligosaccharide, or combinations thereof. In other embodiments, the cancer marker is an N-linked oligosaccharide or a free oligosaccharide.

The term "free oligosaccharide" refers to any oligosaccharide species that is not attached to a protein and includes, without limitation, oligosaccharides attached to lipids.

The term "m/z" refers to the mass-to-charge ratio obtained by dividing the mass of an ion by its charge number.

The term "individual" refers to any animal, preferably a mammal, and more preferably a human.

The term "individual having cancer" refers to an individual that has exhibited one or more symptoms associated with cancer at the time the test sample is obtained, or has previously been diagnosed as having cancer at the time the test sample is obtained.

The term "individual not having cancer" refers to an individual that has not exhibited any symptoms associated with cancer at the time the control sample is obtained, or is in remission from the symptoms associated with cancer at the time the control sample is obtained, or has not exhibited any recurrence of a previously diagnosed cancer at the time the control sample is obtained. As such, an individual not having cancer need not be distinct from an individual having cancer. For example, an individual can provide samples at different times, e.g., once prior to having cancer (control sample) and once while having cancer (test sample), or a control sample can be obtained from an individual in remission or following therapy and compared to a test sample obtained from the same individual at an earlier time, e.g., when the individual had cancer.

The term "exoglycosidase" refers to an enzyme that selectively hydrolyzes a linkage between two monosaccharides. Preferably, the exoglycosidase selectively hydrolyzes a linkage between two monosaccharides present in an oligosaccharide (e.g., O-linked or N-linked oligosaccharide). Suitable exoglycosidases include, without limitation, fucosidases such as $\alpha$1,2-fucosidase, $\alpha$1-3,4-fucosidase, and $\alpha$1,6-fucosidase; galactosidases such as $\alpha$1-3,6-galactosidase, $\beta$1,3-galactosidase, $\beta$1-3,6-galactosidase, and $\beta$1,4-galactosidase; hexosaminidases such as $\alpha$-N-acetyl-galactosaminidase and $\beta$1-2,3,4,6-N-acetyl-glucosaminidase; hexosidases such as $\beta$-glycosidase; mannosidases such as $\alpha$1-2,3-mannosidase, $\alpha$1,6-mannosidase, and $\beta$1,4-mannosidase; neuraminidases such as $\alpha$2-3,6-neuraminidase, $\alpha$2-3,6,8-neuraminidase, $\alpha$2-3,6,8,9-neuraminidase, and $\alpha$2,3-neuraminidase; xylosidases such as $\beta$1,2-xylosidase; and combinations thereof.

As used herein, the term "array" refers to an array of distinct nucleic acids, peptides, polypeptides, proteins, or oligosaccharides immobilized on a solid support or substrate such as paper, a membrane (e.g., nylon), a filter, a chip, a pin, a bead, glass (e.g., a glass slide), or any other suitable solid support. Preferably, the array comprises a plurality of different oligosaccharide species (e.g., O-linked oligosaccharides, N-linked oligosaccharides, free oligosaccharides, etc.) that are coupled to the substrate surface in different known locations.

The term "therapeutically effective amount" refers to the amount of an antibody or other therapeutic agent (e.g., ions, small organic molecules, peptides, proteins, polypeptides, oligosaccharides, etc.) that is capable of achieving a therapeutic effect in a subject in need thereof. For example, a therapeutically effective amount of an antibody can be the amount that is capable of preventing or relieving one or more symptoms associated with cancer. Preferably, the antibody binds to a marker (e.g., unique oligosaccharide species) that is specific to cancer.

The term "stage of cancer" refers to a cancer staging classification system known and widely used by those skilled in the art, such as the classification system devised by the American Joint Committee on Cancer (AJCC). One skilled in the art understands that the staging of a particular type of cancer depends on a number of factors including, without limitation, tumor size, the extent of spreading within the organ and to nearby organs, the extent of spreading to the lymph nodes, and the extent of spreading to distant organs (i.e., metastasis). The AJCC classification system for a particular type of cancer is typically divided into four stages (Stages I-IV), with each stage optionally subdivided into substages (e.g., Stages IIIA, IIIB, and IIIC). As used herein, the term "early stage cancer" refers to a Stage I cancer, but can also refer to a Stage II cancer or a substage of a Stage II cancer (e.g., Stage IIA). The term "late stage cancer" as used herein refers to a Stage III or Stage IV cancer, but can also refer to a Stage II cancer or a substage of a Stage II cancer. One skilled in the art will appreciate that the classification of a Stage II cancer as either an early stage cancer or a late stage cancer depends on the particular type of cancer. For example, the term "early stage ovarian cancer" refers to a Stage I or Stage IIA ovarian cancer and the term "late stage ovarian cancer" refers to a Stage IIB to Stage IV ovarian cancer.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of an antibody or other therapeutic agent for preventing or relieving one or more symptoms associated with cancer.

III. General Overview

The present invention provides methods for identifying oligosaccharides specific to cancer and methods for determining a strain of cancer in an individual. The present invention also provides methods for diagnosing cancer or a stage of cancer in an individual by detecting the presence or absence of specific cancer markers and methods for treating cancer by administering antibodies directed to such markers. In addition, the present invention provides cancer markers comprising O-linked oligosaccharides and kits for diagnosing or treating cancer.

The present invention is based on the discovery that O-linked oligosaccharides released from cell lines or serum are indicators of cancer. Although attempts have been made to analyze differential glycosylation of MUC1 in tumors, cancer cell lines, and transfected epithelial and lyphoblastoid cell lines, they relied upon the use of monoclonal antibodies, lectins, or metabolically radiolabeled carbohydrates. As a result, those studies were severely limited by their inability to show precise differences in glycosylation between normal and cancer mucins due to the difficulty in obtaining sufficient material for detailed structural information. However, the present invention overcomes such limitations through the use of mass spectrometry techniques such as MALDI-Fourier transform mass spectrometry (FTMS) to identify oligosaccharide species in a sample. In particular, the capability of FTMS to provide accurate mass measurements (i.e., <10 ppm routinely, <5 ppm with internal calibration) is critical for obtaining rudimentary oligosaccharide compositions. Furthermore, the methods of the present invention advantageously employ the selective release of oligosaccharides from a sample without the need for a separation step. Such oligosaccharides are particularly useful as markers for detecting cancer in an individual.

IV. Description of the Embodiments

In one aspect, the present invention provides a method for identifying an oligosaccharide specific to cancer, the method comprising:
(a) selectively releasing the oligosaccharides from a test sample, wherein the test sample is a sample from a cancer cell line or an individual having cancer;
(b) obtaining a mass spectrum of the oligosaccharides from the test sample using matrix-assisted laser desorption ionization (MALDI)-Fourier transform mass spectrometry (FTMS); and
(c) comparing the mass spectrum from the test sample to the mass spectrum from a control sample, wherein the oligosaccharide specific to cancer is identified by the presence of a unique oligosaccharide in the mass spectrum from the test sample.

The term "selectively releasing" refers to methods known to one skilled in the art for releasing primarily O-linked oligosaccharides, N-linked oligosaccharides, free oligosaccharides, or a combination thereof from a sample. For example, methods using sodium borohydride ($NaBH_4$) as described in Morelle et al., *Eur. J. Biochemistry*, 252:253-260 (1998) and methods using hydrazine as described in Patel et al., *Biochemistry*, 32:679-693 (1993) are suitable for selectively releasing the O-linked oligosaccharides from a sample. Methods using PNGase F as described in Fan et al., *J. Biol. Chem.*, 272:27058-27064 (1997); Tarentino et al., *Methods Enzymol.*, 230:44-57 (1994); and Trimble et al., *J. Biol. Chem.*, 266:1646-1651 (1991) are suitable for selectively releasing the N-linked oligosaccharides from a sample. Methods for selectively releasing the free oligosaccharides from a sample are described in, e.g., Morelle et al., supra.

With respect to O-linked oligosaccharides, the term "selectively releasing" encompasses the release of at least about 70%, preferably at least about 80%, more preferably at least about 90%, and most preferably at least about 95% of the O-linked oligosaccharides from a sample and the release of less than about 30%, preferably less than about 20%, more preferably less than about 10%, and most preferably less than about 5% of all other species such as non-O-linked oligosaccharides (e.g., N-linked oligosaccharides), proteins, peptides, and nucleic acids from the sample. Similarly, with respect to N-linked oligosaccharides, the term encompasses the release of at least about 70%, preferably at least about 80%, more preferably at least about 90%, and most preferably at least about 95% of the N-linked oligosaccharides from a sample and the release of less than about 30%, preferably less than about 20%, more preferably less than about 10%, and most preferably less than about 5% of all other species such as non-N-linked oligosaccharides (e.g., O-linked oligosaccharides), proteins, peptides, and nucleic acids from the sample. Likewise, with respect to free oligosaccharides, the term encompasses the release of at least about 70%, preferably at least about 80%, more preferably at least about 90%, and most preferably at least about 95% of the free oligosaccharides from a sample and the release of less than about 30%, preferably less than about 20%, more preferably less than about 10%, and most preferably less than about 5% of all other species such as other oligosaccharides, proteins, peptides, and nucleic acids from the sample. One skilled in the art will appreciate that a combination of O-linked, N-linked, and/or free oligosaccharides can be selectively released from a sample.

The term "sample" refers to any biological specimen obtained from an individual. Suitable samples for use in the present invention include, without limitation, whole blood, plasma, serum, saliva, urine, stool, tears, and any other bodily fluid or tissue. The sample can be obtained from the individual by any method known to one skilled in the art. For example, a whole blood sample can be obtained by drawing blood from an individual. Alternatively, a whole blood sample can be obtained from a blood bank or from a physician's office. The term also encompasses any specimen obtained from a cell line including, without limitation, conditioned medium and a cellular extract such as a membrane extract, a cytosolic extract, a nuclear extract, etc.

As used herein, the term "test sample" refers to a sample from a cancer cell line or an individual having cancer. Suitable cancer cell lines include, without limitation, ovarian cancer cell lines such as CaOV-3, OVCAR-3, ES-2, SK-OV-3, SW626, TOV-21G, TOV-112D, OV-90, MDA-H2774, and PA-1; breast cancer cell lines such as MCF7, MDA-MB-231, MDA-MB-468, MDA-MB-361, MDA-MD-453, BT-474, Hs578T, HCC1008, HCC1954, HCC38, HCC1143, HCC1187, HCC1395, HCC1599, HCC1937, HCC2218, Hs574.T, Hs742.T, Hs605.T, and Hs606; lung cancer cell lines such as NCI-H2126, NCI-H1395, NCI-H1437, NCI-H2009, NCI-H1672, NCI-H2171, NCI-H2195, NCI-H1184, NCI-H209, NCI-H2107, and NCI-H128; skin cancer cell lines such as COLO829, TE354.T, Hs925.T, WM-115, and Hs688(A).T; bone cancer cell lines such as Hs919.T, Hs821.T, Hs820.T, Hs704.T, Hs707(A).T, Hs735.T, Hs860.T, Hs888.T, Hs889.T, Hs890.T, and Hs709.T; colon cancer cell lines such as Caco-2, DLD-1, HCT-116, HT-29, and SW480; gastric cancer cell lines such as RF-1; and any other cancer cell line known to one skilled in the art. Cancer cell lines useful in the methods of the present invention can be obtained from, e.g., the American Type Culture Collection (ATCC; Manassas, Va.), the National Cancer Institute, or cancer centers or laboratories such as the University of California at Davis Medical Center. An "individual having cancer" refers to an individual that has exhibited one or more symptoms associated with cancer at the time the test sample is obtained, or has previously been diagnosed as having cancer at the time the test sample is obtained.

As used herein, the term "control sample" refers to a sample from a normal cell line or an individual not having cancer. Suitable normal cell lines include, without limitation, ovarian cell lines such as NOV-31; breast cell lines such as Hs578Bst; peripheral blood cell lines such as NCI-BL2126, NCI-BL1395, NCI-BL1437, NCI-BL2009, NCI-BL2122, NCI-BL2087, NCI-BL1672, NCI-BL2171, NCI-BL2195, NCI-BL1184, NCI-BL209, NCI-BL2107, NCI-BL128, NCI-BL2052, NCI-BL1770, HCC1007BL, HCC1954BL, HCC38BL, HCC1143BL, HCC1187BL, HCC1395BL, HCC1599BL, HCC1937BL, HCC2157BL, HCC2218BL, and COLO829BL; lung cell lines such as Hs888Lu; skin cell lines such as Hs574.Sk, Hs742.Sk, Hs605.Sk, Hs606.Sk, TE353.Sk, Hs925.Sk, Hs919.Sk, Hs821.Sk, Hs820.Sk, Hs704.Sk, Hs707(B).Ep, Hs735.Sk, Hs889.Sk, Hs890.Sk, Hs709.Sk, Hs789.Sk, and Hs814.Sk; colon cell lines such as CCD-18Co; and any other normal cell line known to one skilled in the art. Normal epithelial cell lines can be created from primary human tissue obtained as surgical discards from which primary, untransformed cells can be isolated and cultured (see, e.g., Syed et al., *Cancer Res.,* 61:6768-6776 (2001)). Normal cell lines useful in the methods of the present invention can be obtained from, e.g., ATCC (Manassas, Va.). An "individual not having cancer" refers to an individual that has not exhibited any symptoms associated with cancer at the time the control sample is obtained, or is in remission from the symptoms associated with cancer at the time the control sample is obtained, or has not exhibited any recurrence of a previously diagnosed cancer at the time the control sample is obtained.

One skilled in the art will appreciate that an individual not having cancer need not be distinct from an individual having cancer. For example, an individual can provide samples at different times, e.g., once prior to having cancer (control sample) and once while having cancer (test sample), or a control sample can be obtained from an individual in remission or following therapy and compared to a test sample obtained from the same individual at an earlier time, e.g., when the individual had cancer.

In the methods of the present invention, the mass spectrum of the oligosaccharides (e.g., O-linked, N-linked, and/or free oligosaccharides) from the test sample and the control sample are obtained using mass spectrometry techniques such as matrix-assisted laser desorption ionization (MALDI)-Fourier transform mass spectrometry (FTMS). MALDI is particularly advantageous because it facilitates desorption and ionization of biomolecules such as carbohydrates, nucleic acids, and proteins without their fragmentation. For example, Hillenkamp et al., *Anal. Chem.,* 63:1193A-1203A (1991); Karas et al., *Anal. Chem.,* 60:2299-2301 (1988); and Stahl et al., *Anal. Biochem.,* 223:218-226 (1994) describe the application of MALDI to biomolecules. FTMS is a very high resolution mass spectrometry technique based on the magnetic trapping of ions and the excitation/detection of their cyclotron frequencies. As a result, FTMS can provide accurate mass measurements, i.e., <10 ppm routinely, <5 ppm with internal calibration. The application of MALDI-FTMS to the identification of oligosaccharide species in a sample is described, for example, in Tseng et al., *Anal. Biochem.,* 250:18-28 (1997) and Tseng et al., *Anal. Chem.,* 71:3747-3754 (1999).

As used herein, the term "obtaining a mass spectrum of the oligosaccharides" refers to obtaining an oligosaccharide profile for a sample (i.e., test sample or control sample) that contains either all of the O-linked, N-linked, and/or free oligosaccharide species released from the sample or a fraction thereof. For example, when O-linked oligosaccharides are selectively released and purified by a technique such as solid phase extraction on a porous graphitized carbon (PGC) column, depending on the percentage (e.g., 10%, 20%, 40%) and/or type of solvent (e.g., acetonitrile) used, only a fraction of the released O-linked oligosaccharide species is eluted from the column. A mass spectrum obtained on the fraction can contain, for example, less than 1%, at least 1%, at least 5%, at least 10%, or at least 20% of the released O-linked oligosaccharide species. One skilled in the art will appreciate that the fraction of the released O-linked, N-linked, and/or free oligosaccharide species present in the mass spectrum can also depend on whether the mass spectrum is obtained in the positive mode or the negative mode.

As used herein, the term "comparing the mass spectrum from a test sample to the mass spectrum from a control sample" refers to comparing or aligning the mass spectrum profile from a test sample to the mass spectrum profile from a control sample and determining any similarities and/or differences between the two mass spectrum profiles. One skilled in the art will appreciate that the mass spectrum profile can be a set of peaks, a set of m/z ratios, a set of rudimentary compositions, or in any other format suitable for comparing the oligosaccharides from a test sample to a control sample. The control mass spectrum profile can be obtained at the same time as the test mass spectrum profile or, alternatively, the control mass spectrum profile can be obtained previously and stored, for example, in a database. One skilled in the art will also appreciate that the two mass spectrum profiles can be compared by a computer, e.g., using datasets. In certain instances, a computer software program compares and/or interprets the two mass spectrum profiles, e.g., using peak matching techniques. In certain other instances, an internet application compares and/or interprets the two mass spectrum profiles.

The term "oligosaccharide specific to cancer is identified by the presence of a unique oligosaccharide in the mass spectrum from the test sample" refers to the identification of those O-linked, N-linked, and/or free oligosaccharides whose levels have modulated in the test sample compared to their levels in the control sample. More particularly, the term encompasses any O-linked, N-linked, or free oligosaccharide species that is present in the test sample but is absent from the control sample, any O-linked, N-linked, or free oligosaccharide species whose level is enhanced in the test sample compared to the control sample, any O-linked, N-linked, or free oligosaccharide species whose level is reduced in the test sample compared to the control sample, and any O-linked, N-linked, or free oligosaccharide species that is present in the control sample but is absent from the test sample.

In one embodiment, the method further comprises the step of subjecting the unique oligosaccharide or oligosaccharides to infrared multiphoton dissociation (IRMPD). The use of IRMPD is advantageous over techniques such as collision-induce dissociation (CID) because IRMPD does not limit the m/z range of observed product ions, eliminates the need for matching resonant frequencies, and allows more sequence information to be obtained, typically down to the last residue. As a result, the complete sequencing of even large oligosaccharides can be performed in a single experiment. In another embodiment, the method further comprises the step of digesting the unique oligosaccharides with an exoglycosidase. Preferably, the exoglycosidase selectively hydrolyzes a linkage between two monosaccharides present in the oligosaccharide. Suitable exoglycosidases for use in the present invention include any of the fucosidases, galactosidases, hexosaminidases, hexosidases, mannosidases, neuraminidases, and xylosidases described above or any other exoglycosidase known to one skilled in the art.

In another embodiment, the unique oligosaccharide is an O-linked oligosaccharide selected from the group consisting of a sulfated oligosaccharide, an N-acetylneuraminic acid (NeuAc)-containing oligosaccharide, an N-glycolylneuraminic acid (NeuGc)-containing oligosaccharide, a neutral oligosaccharide, a hexose (Hex)-containing oligosaccharide, a hexuronic acid (HexA)-containing oligosaccharide, and combinations thereof.

In yet another embodiment, the oligosaccharide is specific to any one of the above-described cancers. Preferably, the cancer is ovarian cancer or breast cancer. In certain instances, the test sample from a cancer cell line and/or the control sample from a normal cell line is conditioned medium. In certain other instances, the test sample from an individual having cancer and/or the control sample from an individual not having cancer is serum.

In still yet another embodiment, the present invention provides an antibody that binds specifically to a unique oligosaccharide identified by the above-described method. "Antibody" refers to a polypeptide comprising a framework region from an immunoglobulin gene or fragments thereof that specifically binds and recognizes an antigen such as a unique oligosaccharide of the present invention. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). Light chains are classified as either kappa or lambda. Heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. The remainder of each chain defines a constant region that is conserved and exhibits low variability among different antibodies. Each light chain contains one constant region ($C_L$) and each heavy chain contains three constant regions ($C_H1$, $C_H2$, $C_H3$). Different classes of constant regions in the stem of the antibody generate different isotypes with differing properties based on their amino acid sequence.

Antibodies exist, e.g., as intact immunoglobulins or as a number of well-characterized fragments produced by digestion with various peptidases, referred to herein as "antibody fragments." Thus, for example, pepsin digests an antibody below the disulfide linkages in the hinge region to produce F(ab)$'_2$, a dimer of Fab (fragment, antigen binding) which itself is a light chain joined to $V_H$-$C_H1$ by a disulfide bond. The F(ab)$'_2$ may be reduced under mild conditions to break the disulfide linkage in the hinge region, thereby converting the F(ab)$'_2$ dimer into an Fab' monomer. The Fab' monomer is essentially Fab with part of the hinge region (see, *Fundamental Immunology*, Paul ed., 3d ed., 1993). While various antibody fragments are defined in terms of the digestion of an intact antibody, one of skill in the art will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, any technique known in the art can be used (see, e.g., Kohler & Milstein, *Nature* 256:495-497 (1975); Kozbor et al., *Immunology Today*, 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (see, e.g., U.S. Pat. Nos. 4,816,567 and 4,946,778) can be adapted to produce antibodies directed to the oligosaccharides of the present invention. In addition, transgenic mice or other organisms such as other mammals may be used to express humanized or human antibodies (see, e.g., U.S. Pat. Nos. 5,545,807; 5,545,806; 5,569,825; 5,625,126; 5,633,425; 5,661,016; Marks et al., *Biotechnology*, 10:779-783 (1992); Lonberg et al., *Nature*, 368:856-859 (1994); Morrison, *Nature*, 368:812-13 (1994); Fishwild et al., *Nature Biotechnology*, 14:845-51 (1996); Neuberger, *Nature Biotechnology*, 14:826 (1996); and Lonberg & Huszar, *Intern. Rev. Immunol.*, 13:65-93 (1995)). Alternatively, phage display technology can be used to identify antibodies and heteromeric Fab fragments that specifically bind to selected antigens (see, e.g., McCafferty et al., *Nature*, 348:552-554 (1990); Marks et al., *Biotechnology*, 10:779-783 (1992)). Antibodies can also be made bispecific, i.e., able to recognize two different antigens (see, e.g., WO 93/08829; Traunecker et al., *EMBO J.*, 10:3655-3659 (1991); and Suresh et al., *Methods in Enzymology*, 121:210 (1986)). Antibodies can also be heteroconjugates, e.g., two covalently joined antibodies, or immunotoxins (see, e.g., U.S. Pat. No. 4,676,980; PCT Publications WO 91/00360 and WO 92/200373; and EP 03089).

A "chimeric antibody" is an antibody molecule in which (a) the constant region, or a portion thereof, is altered, replaced, or exchanged so that the antigen binding site (variable region) is linked to a constant region of a different or altered class, effector function, and/or species, or an entirely different molecule which confers new properties to the chimeric antibody, e.g., an enzyme, toxin, hormone, growth factor, drug, etc.; or (b) the variable region, or a portion thereof, is altered, replaced, or exchanged with a variable region having a different or altered antigen specificity. For example, a chimeric antibody can comprise mouse protein sequence in the variable region and human protein sequence in the constant region. A "humanized antibody" comprises even fewer mouse protein sequence in the variable region than chimeric antibodies. Such mouse protein sequence has been replaced by human protein sequence.

In certain instances, the antibody further comprises a detectable label attached thereto. Examples of detectable labels include, without limitation, fluorescein, rhodamine, Texas Red, Cy2, Cy3, Cy5, biotin, horseradish peroxidase, and alkaline phosphatase. One skilled in the art will know of additional detectable labels as well as suitable methods for conjugating a particular detectable label to the antibody.

In a further embodiment, the present invention provides a method for treating cancer in an individual in need thereof, the method comprising:

administering to the individual a therapeutically effective amount of an antibody that binds specifically to a unique oligosaccharide.

In certain instances, a therapeutically effective amount of an antibody can be the amount that is capable of preventing or relieving one or more symptoms associated with cancer. Preferably, the antibody binds to a unique oligosaccharide species that is specific to cancer or to a particular type of cancer such as ovarian cancer or breast cancer.

In another aspect, the present invention provides a method for determining a strain of cancer in an individual, the method comprising:

(a) obtaining a mass spectrum of the oligosaccharides from a sample from the individual using MALDI-FTMS, wherein the oligosaccharides have been selectively released from the sample; and (b) comparing the mass spectrum from the sample to a mass spectrum profile from at least one known strain of cancer, wherein the strain of cancer is determined by a similarity between the mass spectrum from the sample and the mass spectrum profile from one of the known strains of cancer.

The term "strain of cancer" refers to a member of a group of cancers of the same type (e.g., ovarian cancer), but having distinctive characteristics (e.g., different mass spectrum profile). In one embodiment, the strain of cancer is a strain of ovarian cancer or breast cancer. A variety of ovarian cancer strains are known to those skilled in the art and include, without limitation, CaOV-3, OVCAR-3, ES-2, SK-OV-3, SW626, TOV-21G, TOV-112D, OV-90, MDA-H2774, and PA-1. A variety of breast cancer strains are known to those skilled in the art and include, without limitation, MCF7, MDA-MB-231, MDA-MB-468, MDA-MB-361, MDA-MD-453, BT-474, Hs578T, HCC1008, HCC1954, HCC38, HCC1143, HCC1187, HCC1395, HCC1599, HCC1937, HCC2218, Hs574.T, Hs742.T, Hs605.T, and Hs606.

As used herein, the term "strain of cancer is determined by a similarity between the mass spectrum from the sample and the mass spectrum profile from one of the known strains of cancer" refers to the determination of whether the mass spectrum from the sample is at least about 70%, preferably at least about 80%, more preferably at least about 90%, and most preferably at least about 95% identical to the mass spectrum profile from one of the known strains of cancer. Preferably, the mass spectrum from the sample is most similar to the mass spectrum profile from one of the known strains of cancer. However, one skilled in the art will appreciate that the mass spectrum from the sample can be similar to the mass spectrum profile from more than one of the known strains of cancer. In these instances, other factors such as comparing the levels (e.g., peak magnitude) of particular species present in the mass spectrum profiles can be used to determine the strain of cancer in the individual.

In yet another aspect, the present invention provides a method for diagnosing cancer in an individual, the method comprising:

detecting the presence or absence of a unique oligosaccharide in a sample from the individual, wherein the presence of the unique oligosaccharide indicates that the individual has cancer.

In one embodiment, the unique oligosaccharide is selected from the group consisting of an O-linked oligosaccharide, an N-linked oligosaccharide, a free oligosaccharide, and combinations thereof. In certain instances, detecting the unique oligosaccharide comprises: (a) obtaining a mass spectrum of the oligosaccharides from a sample from the individual using MALDI-FTMS, wherein the oligosaccharides have been selectively released from the sample; and (b) determining the presence of the unique oligosaccharide in the mass spectrum. In certain other instances, detecting the unique oligosaccharide comprises contacting the sample with an antibody that binds specifically to the unique oligosaccharide.

In still yet another aspect, the present invention provides a method for diagnosing cancer in an individual, the method comprising:

(a) obtaining a mass spectrum of the oligosaccharides from a sample from the individual using MALDI-FTMS, wherein the oligosaccharides have been selectively released from the sample; and (b) comparing the mass spectrum from the sample to the mass spectrum from a control sample, wherein a higher ratio of NeuGc-containing O-linked oligosaccharides to NeuAc-containing O-linked oligosaccharides in the sample relative to the control sample indicates that the individual has cancer.

Figure 14:
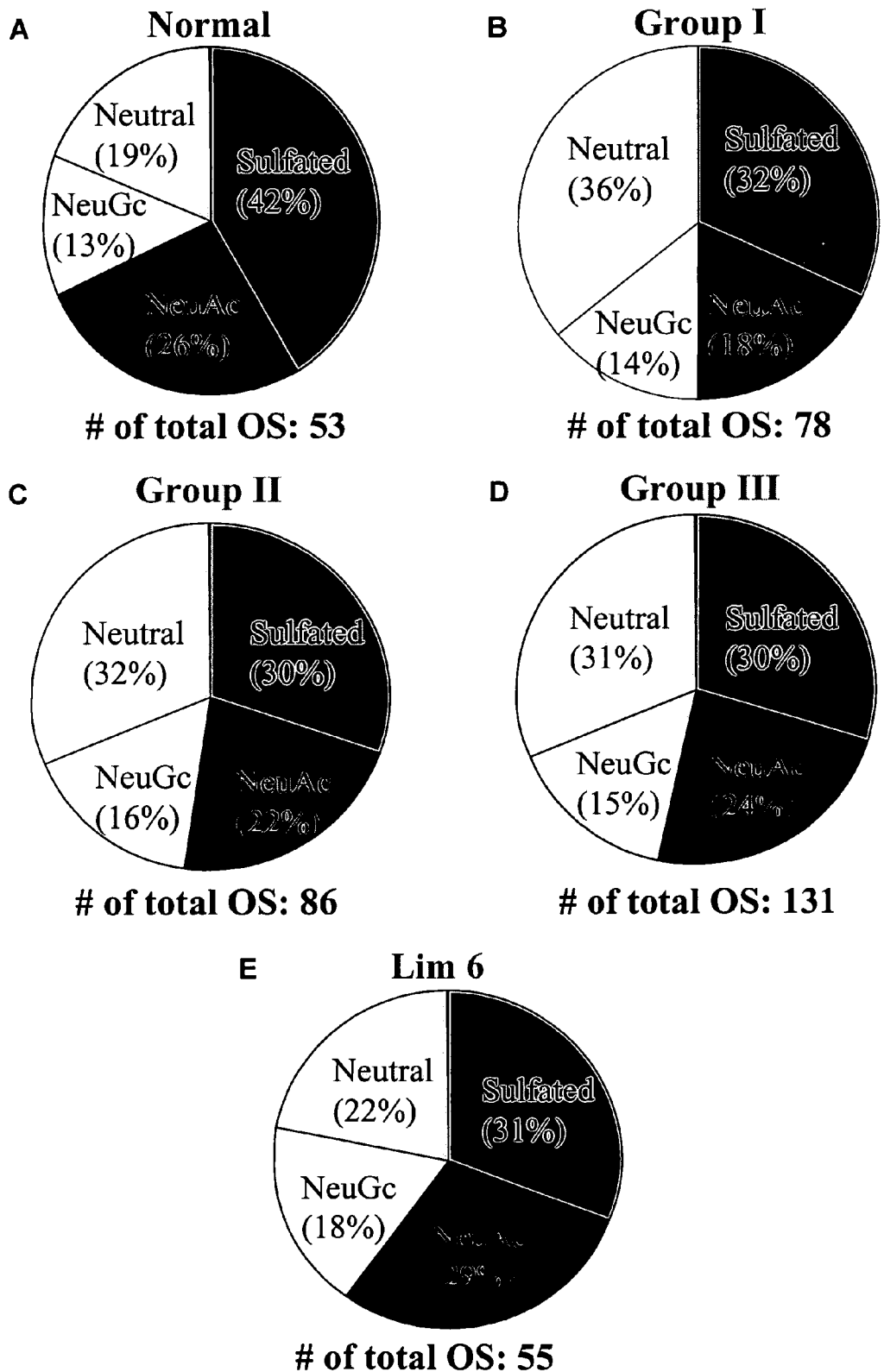
FIG. 14 shows the percentage of each class of O-linked oligosaccharide identified in normal (A), Group I (B), Group II (C), Group III (D), and Lim 6 (E) serum samples.

In one embodiment, the cancer is an adenocarcinoma such as ovarian cancer or breast cancer. In another embodiment, the sample is serum. In certain instances, a comparison of the mass spectrum from the sample to the mass spectrum from the control sample comprises calculating a ratio of NeuGc-containing O-linked oligosaccharides to NeuAc-containing O-linked oligosaccharides in the mass spectrum from the sample and comparing the calculated ratio to a ratio of NeuGc-containing O-linked oligosaccharides to NeuAc-containing O-linked oligosaccharides calculated for the control sample. As used herein, the term "calculating a ratio of NeuGc-containing O-linked oligosaccharides to NeuAc-containing O-linked oligosaccharides" refers to determining the number of NeuGc-containing and NeuAc-containing O-linked oligosaccharide species present in the mass spectrum profile and dividing the number of NeuGc-containing O-linked oligosaccharide species by the number of NeuAc-containing O-linked oligosaccharide species. However, one skilled in the art will know of other methods for calculating the NeuGc/NeuAc ratio including, for example, the use of an algorithm. The NeuGc/NeuAc ratio for the control sample and the sample from an individual can be obtained at the same time or, alternatively, the control NeuGc/NeuAc ratio can be obtained previously and stored, for example, in a database. Example 8 and FIG. 14 illustrate a comparison of the NeuGc/NeuAc ratios between a control (i.e., normal) sample and a series of samples from individuals (i.e., Groups I-III, Lim 6).

In a further aspect, the present invention provides a method for diagnosing cancer in an individual, the method comprising:

(a) obtaining a mass spectrum of the oligosaccharides from a sample from the individual using MALDI-FTMS, wherein the oligosaccharides have been selectively released from the sample; and (b) comparing the mass spectrum from the sample to the mass spectrum from a control sample, wherein a lower percentage of sulfated O-linked oligosaccharides in the sample relative to the control sample indicates that the individual has cancer.

In one embodiment, the cancer is an adenocarcinoma such as ovarian cancer or breast cancer. In another embodiment, the sample is serum. In certain instances, a comparison of the mass spectrum from the sample to the mass spectrum from the control sample comprises calculating a percentage of sulfated O-linked oligosaccharides in the mass spectrum from the sample and comparing the calculated percentage to a percentage of sulfated O-linked oligosaccharides calculated for the control sample. As used herein, the term "calculating a percentage of sulfated O-linked oligosaccharides" refers to determining the number of sulfated O-linked oligosaccharide species and the total number of O-linked oligosaccharide species present in the mass spectrum profile and dividing the number of sulfated O-linked oligosaccharide species by the total number of O-linked oligosaccharide species. The sulfated/total O-linked oligosaccharide ratio can then be converted into a percentage by multiplying the ratio by 100. However, one skilled in the art will know of other methods for calculating the O-linked oligosaccharide percentage including, for example, the use of an algorithm. Preferably, the total number of O-linked oligosaccharide species present in the mass spectrum profile comprises sulfated O-linked oligosaccharides, NeuGc-containing O-linked oligosaccharides, NeuAc-containing O-linked oligosaccharides, and/or neutral O-linked oligosaccharides. The O-linked oligosaccharide percentage for the control sample and the sample from an individual can be obtained at the same time or, alternatively, the control sulfated O-linked oligosaccharide percentage can be obtained previously and stored, for example, in a database. Example 8 and FIG. 14 illustrate a comparison of the sulfated O-linked oligosaccharide percentages between a control (i.e., normal) sample and a series of samples from individuals (i.e., Groups I-III, Lim 6).

In another aspect, the present invention provides a method for diagnosing cancer in an individual, the method comprising:
(a) obtaining a mass spectrum of the oligosaccharides from a sample from the individual, wherein the oligosaccharides have been selectively released from the sample; and
(b) determining the presence or absence of a cancer marker selected from the group consisting of a sulfated oligosaccharide, an N-acetylneuraminic acid (NeuAc)-containing oligosaccharide, an N-glycolylneuraminic acid (NeuGc)-containing oligosaccharide, a neutral oligosaccharide, a hexose (Hex)-containing oligosaccharide, a hexuronic acid (HexA)-containing oligosaccharide, and combinations thereof in the mass spectrum, wherein the presence of the cancer marker indicates that the individual has cancer.

In certain instances, the cancer is an adenocarcinoma such as ovarian cancer or breast cancer. Preferably, the sample is serum. In preferred embodiments of the present invention, the cancer marker is an O-linked oligosaccharide. In other embodiments, the cancer marker is an N-linked oligosaccharide. In yet other embodiments, the cancer marker is a free oligosaccharide.

In one embodiment, the sulfated oligosaccharide has a composition selected from the group consisting of 1 HexNAc:1 Hex:1 $SO_3H$; 1 HexNAc:3 Hex:1 Fuc:1 $SO_3H$; 2 HexNAc:1 Hex:2 Fuc:1 $SO_3H$; 2 HexNAc:3 Hex:1 $SO_3H$; 4 HexNAc:1 Hex:1 $SO_3H$; 2 HexNAc:2 Hex:2 Fuc:1 $SO_3H$; 5 HexNAc:1 Hex:1 Fuc:1 $SO_3H$; and combinations thereof. In another embodiment, the NeuAc-containing oligosaccharide has a composition selected from the group consisting of 1 HexNAc:1 Hex:1 NeuAc; 1 HexNAc:2 Hex:1 NeuAc; 2 HexNAc:1 NeuAc:1 Fuc; 2 HexNAc:1 Hex:1 NeuAc; 1 HexNAc:3 Hex:1 NeuAc; 3 HexNAc:1 NeuAc:3 Fuc; and combinations thereof. In yet another embodiment, the NeuGc-containing oligosaccharide has a composition selected from the group consisting of 1 HexNAc:1 Hex:1 NeuGc:1 Fuc; 1 HexNAc:2 Hex:1 NeuGc; 2 HexNAc:1 NeuGc:1 Fuc; 3 HexNAc:1 NeuGc; 1 HexNAc:2 Hex:1 NeuGc:1 Fuc; 3 HexNAc:4 Hex:1 NeuGc; and combinations thereof. In still yet another embodiment, the neutral oligosaccharide has a composition selected from the group consisting of 1 HexNAc:2 Fuc; 2 HexNAc:2 Fuc; 2 HexNAc:1 Hex:1 Fuc; 4 HexNAc; 1 HexNAc:2 Hex:2 Fuc; 4 HexNAc:1 Hex; 1 HexNAc:3 Hex:2 Fuc; 1 HexNAc:4 Hex:1 Fuc; 3 HexNAc:1 Hex:2 Fuc; 2 HexNAc:4 Hex:1 Fuc; 6 HexNAc; 3 HexNAc:3 Hex:2 Fuc; 4 HexNAc:3 Hex:1 Fuc; and combinations thereof. In an additional embodiment, the Hex-containing oligosaccharide has a composition selected from the group consisting of 2 Hex; 1 HexNAc:1 Hex; 3 Hex; 1 HexNAc:2 Hex; 3 Hex:1 HexNAc; 1 Hex*:2 Hex:1 HexNAc; 4 Hex:1 HexNAc; 3 Hex:2 HexNAc; 1 Hex*:2 Hex:2 HexNAc; 4 Hex:2 HexNAc; 1 Hex*:3 Hex:2 HexNAc; 5 Hex:2 HexNAc; 4 Hex:3 HexNAc; 5 Hex:3 HexNAc; 1 Hex*:4 Hex:3 HexNAc; 2 Hex*:3 Hex:1 HexNAc; and combinations thereof. In a further embodiment, the HexA-containing oligosaccharide has a composition selected from the group consisting of m/z 221+$[HexA]_1$; m/z 221+$[HexA]_2$; m/z 221+$[HexA]_3$; m/z 221+$[HexA]_4$; m/z 221+$[HexA]_5$; m/z 221+$[HexA]_6$; m/z 221+$[HexA]_7$; m/z 361+$[HexA]_1$; m/z 361+$[HexA]_2$; m/z 361+$[HexA]_3$; m/z 361+$[HexA]_4$; m/z 361+$[HexA]_1$; m/z 361+$[HexA]_5$; m/z 361+$[HexA]_6$; m/z 551+$[HexA]_1$; m/z 551+$[HexA]_2$; m/z 551+$[HexA]_3$; m/z 551+$[HexA]_4$; m/z 551+$[HexA]_5$; m/z 555+$[HexA]1$; m/z 555+$[HexA]_2$; m/z 555+$[HexA]_3$; m/z 604+$[HexA]_1$; m/z 604+$[HexA]_2$; m/z 604+$[HexA]_3$; m/z 604+$[HexA]_4$; and combinations thereof.

In yet another aspect, the present invention provides a method for diagnosing a stage of cancer in an individual, the method comprising:
(a) obtaining a mass spectrum of the oligosaccharides from a sample from the individual, wherein the oligosaccharides have been selectively released from the sample;
(b) determining the presence or absence of a first cancer marker in the mass spectrum, wherein the first cancer marker is selected from the group consisting of 1 HexNAc:1 Hex:1 NeuAc; 2 HexNAc:1 NeuAc:1 Fuc; 1 HexNAc:3 Hex:1 NeuAc; 1 HexNAc:2 Hex:1 NeuGc; 3 HexNAc:1 NeuGc; 1 HexNAc:2 Hex:1 NeuGc:1 Fuc; 1 HexNAc:3 Hex:1 Fuc:1 $SO_3H$; 2 HexNAc:1 Hex:2 Fuc:1 $SO_3H$; 2 HexNAc:3 Hex:1 $SO_3H$; 4 HexNAc:1 Hex:1 $SO_3H$; 5 HexNAc:1 Hex:1 Fuc:1 $SO_3H$; 2 HexNAc:2 Fuc; 2 HexNAc:1 Hex:1 Fuc; 4 HexNAc; 4 HexNAc:1 Hex; 1 HexNAc:3 Hex:2 Fuc; 1 HexNAc:4 Hex:1 Fuc; 3 HexNAc:1 Hex:2 Fuc; 2 HexNAc:4 Hex:1 Fuc; and combinations thereof; and
(c) determining the presence or absence of a second cancer marker in the mass spectrum, wherein the second cancer marker is selected from the group consisting of 1 HexNAc:2 Hex:1 NeuAc; 2 HexNAc:1 Hex:1 NeuAc; 3 HexNAc:1 Hex:1 NeuAc:3 Fuc; 1 HexNAc:1 Hex:1 NeuGc:1 Fuc; 2 HexNAc:1 NeuGc:1 Fuc; 3 HexNAc:4 Hex:1 NeuGc; 1 HexNAc:1 Hex:1 $SO_3H$; 2 HexNAc:2 Hex:2 Fuc:1 $SO_3H$; 1 HexNAc:2 Fuc; 1 HexNAc:2 Hex:2 Fuc; 6 HexNAc; 3 HexNAc:3 Hex:2 Fuc; 4 HexNAc:3 Hex:1 Fuc; and combinations thereof, wherein the presence of the first cancer marker and the absence of the second cancer marker indicates that the individual has an early stage cancer and wherein the presence of the second cancer marker indicates that the individual has a late stage cancer.

In one embodiment, the early stage cancer is an early stage ovarian cancer. In certain instances, the early stage ovarian cancer is associated with low CA 125 levels. In another embodiment, the late stage cancer is a late stage ovarian cancer. In certain instances, the late stage ovarian cancer is associated with high CA 125 levels. As used herein, the term "early stage ovarian cancer" refers to a Stage I or Stage IIA ovarian cancer and the term "late stage ovarian cancer" refers to a Stage IIB to Stage IV ovarian cancer. Example 9 illustrates the presence or absence of each of the above-mentioned cancer markers in early stage ovarian cancer and late stage ovarian cancer.

In still yet another aspect, the present invention provides a cancer marker comprising an O-linked oligosaccharide having a composition selected from the group consisting of 1 HexNAc:1 Hex: 1 $SO_3H$; 1 HexNAc:3 Hex:1 Fuc:1 $SO_3H$; 2 HexNAc:1 Hex:2 Fuc:1 $SO_3H$; 2 HexNAc:3 Hex:1 $SO_3H$; 4 HexNAc:2 Hex:1 $SO_3H$; 2 HexNAc:2 Hex:2 Fuc:1 $SO_3H$; 5 HexNAc:1 Hex:1 Fuc:1 $SO_3H$; 1 HexNAc:1 Hex:1 NeuAc; 1 HexNAc:2 Hex:1 NeuAc; 2 HexNAc:1 NeuAc:1 Fuc; 2 HexNAc:1 Hex:1 NeuAc; 1 HexNAc:3 Hex:1 NeuAc; 3 HexNAc:1 Hex:1 NeuAc:3 Fuc; 1 HexNAc:1 Hex:1 NeuGc:1 Fuc; 1 HexNAc:2 Hex:1 NeuGc; 2 HexNAc:1 NeuGc:1 Fuc; 3 HexNAc:1 NeuGc; 1 HexNAc:2 Hex:1 NeuGc:1 Fuc; 3 HexNAc:4 Hex:1 NeuGc; 1 HexNAc:2 Fuc; 2 HexNAc:2 Fuc; 2 HexNAc:1 Hex:1 Fuc; 4 HexNAc; 1 HexNAc:2 Hex:2 Fuc; 4 HexNAc:1 Hex; 1 HexNAc:3 Hex:2 Fuc; 1 HexNAc:4 Hex:1 Fuc; 3 HexNAc:1 Hex:2 Fuc; 2 HexNAc:4 Hex:1 Fuc; 6 HexNAc; 3 HexNAc:3 Hex:2 Fuc; 4 HexNAc:3 Hex:1 Fuc; 2 Hex; 1 HexNAc:1 Hex; 3 Hex; 1 HexNAc:2 Hex; 3 Hex:1 HexNAc; 1 Hex*:2 Hex:1 HexNAc; 4 Hex:1 HexNAc; 3 Hex:2 HexNAc; 1 Hex*:2 Hex:2 HexNAc; 4 Hex:2 HexNAc; 1 Hex*:3 Hex:2 HexNAc; 5 Hex:2 HexNAc; 4 Hex:3 HexNAc; 5 Hex:3 HexNAc; 1 Hex*:4 Hex:3 HexNAc; 2 Hex*:3 Hex:1 HexNAc; m/z 221+$[HexA]_1$; m/z 221+$[HexA]_2$; m/z 221+$[HexA]_3$; m/z 221+$[HexA]_4$; m/z 221+$[HexA]_5$; m/z 221+$[HexA]_6$; m/z 221+$[HexA]_7$; m/z 361+$[HexA]_1$; m/z 361+$[HexA]_2$; m/z 361+$[HexA]_3$; m/z 361+$[HexA]_4$; m/z 361+$[HexA]_5$; m/z 361+$[HexA]_6$; m/z 551+$[HexA]_1$; m/z 551+$[HexA]_2$; m/z 551+$[HexA]_3$; m/z 551+$[HexA]_4$; m/z 551+$[HexA]_5$; m/z 555+$[HexA]_1$; m/z 555+$[HexA]_2$; m/z 555+$[HexA]_3$; m/z 604+$[HexA]_1$; m/z 604+$[HexA]_2$; m/z 604+$[HexA]_3$; m/z 604+$[HexA]_4$; and combinations thereof.

In one embodiment, the present invention provides an antibody that binds specifically to an O-linked oligosaccharide. In certain instances, the antibody further comprises a detectable label attached thereto. Examples of detectable labels include, without limitation, fluorescein, rhodamine, Texas Red, Cy2, Cy3, Cy5, biotin, horseradish peroxidase, and alkaline phosphatase.

In a further aspect, the present invention provides a method for treating cancer in an individual in need thereof, the method comprising:
   administering to the individual a therapeutically effective amount of an antibody that binds specifically to a cancer marker.

In a preferred embodiment, a therapeutically effective amount of an antibody can be the amount that is capable of preventing or relieving one or more symptoms associated with cancer.

In yet another embodiment, the present invention provides an oligosaccharide array comprising a plurality of O-linked oligosaccharides immobilized on a solid support. Examples of suitable solid supports include, without limitation, paper, membranes, filters, chips, pins, and glass.

In another aspect, the present invention provides a kit for diagnosing cancer in an individual, the kit comprising:
   (a) an array comprising a plurality of cancer markers;
   (b) a plurality of antibodies that binds specifically to the plurality of cancer markers on the array; and
   (c) directions for use of the array and the plurality of antibodies with a sample from the individual.

In certain instances, the plurality of antibodies further comprises a detectable label attached thereto. Examples of detectable labels are described above.

In yet another aspect, the present invention provides a kit for treating cancer in an individual in need thereof, the kit comprising:
   (a) an antibody that binds specifically to a cancer marker; and
   (b) directions for use of the antibody.

V. Glycobiology of Cancer

Glycosylation is highly sensitive to the biochemical environment and has been implicated in both development and disease (Dennis et al., *BioEssays*, 21:412-421 (1999)). Indeed, cancer cells produce significantly different oligosaccharides than normal cells (Hollingsworth et al., id; Dall'Olio et al., *Glyconj. J.*, 18:841-850 (2001); Brockhausen, *Biochim. Biophys. Acta*, 1473:67-95 (1999); Yogeeswaran, *Cancer Markers: Diagnostic and Developmental Significance*, Humana Press, Clifton, N.J., (1980); Yamori et al., *Cancer Res.*, 47:2741-2747 (1987); Gorelik et al., *Cancer Metastasis Rev.*, 20:245-277 (2001)). In addition, specific glycoproteins may be produced in varying rates depending on the cancer cell type.

Analysis of mucins and their oligosaccharides are complicated by their size and heterogeneity. CA 125 is a typical mucin glycoprotein in terms of its size and heterogeneity and serves as a useful illustration of the complexity of mucins and the difficulty in analyzing them. Despite the widespread use of CA 125 as a cancer marker and its relatively early discovery in 1983, many of its O- and N-glycan structures have only recently been characterized (Wong et al., *J. Biol. Chem.*, 278:28619-28634 (2003)). The core protein sequence of CA 125 comprises over 10,000 amino acids and has a molecular weight of about 2.5 million Da (O'Brien et al., *Tumour Biol.*, 12:154-169 (2002)). The carbohydrate content of CA 125, based on the mass, is estimated to be at least 25%, with the majority being O-linked glycans. The added mass indicates that the average molecular weight of CA125 is actually about 3.5 million Da.

High levels of mucin production are often found in adenocarcinomas. There are two main classes of mucins: secreted and cell-surface associated. Both classes share many structural features. Because glycosylation is highly sensitive to the biochemical environment, cancer cells produce significantly different oligosaccharides than normal cells. Mucins from cancer cells are therefore not only over-expressed but are also aberrantly glycosylated. Although the heavy O-glycosylation of mucins makes them unwieldy from an analytical point of view, aberrantly glycosylated mucins can serve as sensitive indicators of differentiation-dependent fluctuations in the cellular glycosylation machinery. Mucin over-expression and aberrantly glycosylated forms of mucin typically arise as a consequence of the deregulation of expression of mucin core proteins and the enzymes that modify them during the transformation of tumor cells.

It has been estimated that 50% of all proteins are glycosylated, making it the most common form of post-translational modification. There are two types of glycosylation: O- and N-glycosylation. N-glycosylation is initiated by the addition of an N-acetylglucosamine (GlcNAc) to an asparagine residue of a protein. A second GlcNAc and a trimannosyl chitobiosyl core structure are then linked to the protein via the initial GlcNAc.

The structural complexity of O-glycosylation far exceeds that of N-glycosylation. O-glycans are typically linked to a serine or threonine residue of a protein. The most ubiquitous type of initial O-glycosylation occurs by the addition of N-acetylgalactosamine (GalNAc). For example, heavily O-glycosylated proteins such as mucins contain clusters of GalNAc-based glycans in repetitive Ser- and Thr-rich peptide motifs. However, unlike N-glycans, there at least eight core O-glycan structures are known (FIG. 1). Core 1 and core 2 are the most common. Core 3 and core 4 are associated with specific tissues, while other core structures are either present in small amounts or are found in very specific types of cancer cells. Core 1 and core 2 are characterized by a Galβ1-3 linkage to the initial GalNAc. Core 2 is the result of a further addition of a GlcNAc to the initial GalNAc via a β1-6 linkage.

In normal cells, a backbone region on an O-glycan structure is formed by the addition of repetitive disaccharide elements such as Galβ1-4GlcNAc or Galβ1-3GlcNAc to produce polylactosamine-type structures with as many as 20 monosaccharide residues. These repeating units are then truncated by other types of monosaccharide residues including, but not limited to, fucoses and sialic acids (e.g., N-acetylneuraminic acid (NeuAc); FIG. 2). The sequence of glycosylation events occur in the presence of many competing glycosyl transferases that yield precise linkages between oligosaccharides. As the depletion or over-expression of a small number of glycosyl transferases can greatly modify the structure of the resulting oligosaccharides, glycosylation is highly sensitive to the biochemical environment.

In cancer, the associated O-glycan structures exhibit striking alterations compared to normal cells. For example, truncated O-glycans are frequently observed (Van den Steen et al., *Crit. Rev. Biochem. Mol. Biol.*, 33:151-208 (1998)). Studies on breast cancer cells revealed that Core 2-based polylactosamines on MUC1 was absent on most of the cancer cells due to the reduction and/or absence of UDP-GlcNAc/Core1 β6-N-acetylglucosaminyltrasferase (C2GnT) activity, which is responsible for the formation of core 2 by the addition of βGlcNAc to the 6 position of the initial GalNAc residue (Hanisch et al., *Eur. J. Biochem.*, 236:318-327 (1996); Lloyd et al., *J. Biol. Chem.*, 271:33325-33334 (1996); Brockhausen et al., *Eur. J. Biochem.*, 233:607-617 (1995)). As a result, precursor structures such as GalNAc-Ser/Thr and Galβ1-3GalNAc-Ser/Thr build-up and become substrates for sialyltransferases. The addition of sialic acid is an important function in normal cells. The number of different sialyltransferases cloned so far approaches 20, which is a testament to the importance of the reaction (Harduin-Lepers et al., *Biochemie*, 83:727-737 (2001)). A sialic acid acts as a biosynthetic stop that prevents the further extension of the glycan chain. For example, the over-expression of α3- and α6-sialyltransferases results in the production of mucins with short glycan chains and a high degree of sialylation. Such short-chained oligosaccharides have attracted considerable interest as clinically important tumor antigens and include the the well-known sialyl-Tn (STn) antigen (Siaα2,6-GalNAc-O-Ser/Thr) (Dall'Olio et al., *Glyconj. J.*, 18:841-850 (2001); Yonezawa et al., *Am. J. Clin. Pathol.*, 98:167-174 (1992); Itzkowitz et al., *Cancer Res.*, 49:197-204 (1989); Thor et al., *Cancer Res.*, 46:3118-3124 (1986); Werther et al., *Br. J. Cancer*, 69:613-616 (1994)). Most adenocarcinomas including breast and ovarian express STn. In contrast, STn is rarely found in normal tissues. Other short chain oligosaccharides include sialyl-Lewis x (Si-Le$^x$, NeuAcα2-3Galβ1-4[Fucα1-3]GlcNAc) and sialyl-Lewis a (Si-Le$^a$, NeuAcα2-3Galβ1-3[Fucα1-4]GlcNAc), which are used to monitor gastrointestinal and pancreatic cancers (Fernandez-Rodriguez et al., *Glyconj. J.*, 18:925-930 (2001)).

Another alteration in the glycosylation of proteins in cancer cells is the addition of a type of sialic acid not normally found in humans, i.e., N-glycolylneuraminic acid (NeuGc) (FIG. 2). NeuGc is abundant in other mammals such as the great apes but is found only in trace amounts in humans (Varki, *Biochimie*, 83:615-622 (2001); Malykh et al., *Biochimie*, 83:623-634 (2001)). In fact, the amount of NeuGc in humans is usually less than 1% of total sialic acids. NeuGc is believed not to originate in humans but is incorporated metabolically. Although elevated expression of NeuGc in cells from tumor tissues and in patients with cancer have been reported, the presence of increased levels of NeuGc in cancer tissues is still controversial (Tangvoranuntakul et al., *Proc. Natl. Acad. Sci. USA.*, 100:12045-12050 (2003)). The problem in verifying the presence of the NeuGc lies in the method of analysis, as most studies monitor NeuGc levels using only antibody assays. However, NeuGc residues have been detected by liquid chromatography-mass spectrometry (LC-MS) from the sialidase treatment of mucins from the ascites fluid of a patient with an endometrium carcinoma (Devine et al., *Cancer Res.*, 51:5826-5836 (1991)) and by gas chromatography (GC)-MS from mucins isolated from a ductal mammary carcinoma (Hanisch et al., *Eur. J. Biochem.*, 236:318-327 (1996)).

A difference in the amount of sulfated oligosaccharides between normal cells and cancer cells represents yet another alteration in the glycosylation of proteins in cancer cells. Sulfated oligosaccharides typically add a net negative charge to glycoproteins such as mucins. The sulfate group on the oligosaccharide masks underlying antigens and protects mucin from degradation by bacterial glycosidases. Sulfated oligosaccharides are also involved in cell adhesion, growth factor presentation, cell signaling, and inflammation (Delcommenne et al., *Glycobiology*, 12:613-622 (2002)). In the biosynthesis of oligosaccharides, sulfation can block pathways and turn off branching and elongation reactions (Brockhausen, *Biochem. Soc. Trans.*, 31:318-325 (2003)). The sulfate content of mucins has been reported to decrease in cancerous colon mucosa (Yamori et al., *Cancer Res.*, 47:2741-2747 (1987); Raouf et al., *Clin. Sci*, 83:623-626 (1992)) and in breast cancer cells (Brockhausen et al., *Eur. J. Biochem.*, 233:607-617 (1995)). Specific mucin-degrading sulfatases have also been isolated, indicating that the hyperactivity of these enzymes results in the under-sulfation of mucins (Corfield et al., *Glyconj. J.*, 13:809-822 (1996)).

VI. Mass Spectrometry of Oligosaccharides

The complexity of oligosaccharides is readily apparent in the more than 15 million tetrasaccharides with variations in linkages, branching, and anomericity that can be assembled from nine common monosaccharides found in humans. In addition, many common monosaccharides are stereoisomers with identical masses. Several strategies have been developed for the structural elucidation of oligosaccharides that employ nuclear magnetic resonance (NMR) and mass spectrometry. NMR is the only spectroscopic method that provides the complete structure of an oligosaccharide; however, limitations in sensitivity preclude the use of NMR to all but the most abundant species of oligosaccharides (Plancke et al., *Eur. J. Biochem.*, 231:434-439 (1995); Strecker et al., *Glycobiology*, 5:137-146 (1995); Dell et al., *Carbohydr. Res.*, 115:41-52 (1983)). The analysis is also complex and requires lengthy measurements and interpretation of the NMR spectrum. Furthermore, because oligosaccharide samples are often found to be highly heterogeneous, containing numerous components with abundances that can vary by several orders of magnitudes, rigorous separation is often required for unambiguous elucidation by NMR.

The structural heterogeneity, complexity, and sample limitations make the analyses of oligosaccharides well suited for mass spectrometry (MS). For example, mass spectrometry has been used to identify O-linked oligosaccharides from mucins such as MUC2 (Alving et al., *J. Mass Spectrom.*, 34:395-407 (1999)) and MUC4 (Alving et al., *J. Mass Spectrom.*, 33:1124-1133 (1998)). Fast atom bombardment (FAB)-MS and gas chromatography (GC)-MS have also been used to identify the O-linked oligosaccharides of MUC1 that are associated with breast cancer (Hanisch et al., *Eur. J. Biochem.*, 236:318-327 (1996)). In addition, the N- and O-glycans associated with CA 125 (MUC16) have been characterized by mass spectrometry (Wong et al., *J. Biol. Chem.*, 278:28619-28634 (2003)).

The availability of matrix-assisted laser desorption ionization (MALDI) (Karas et al., *Anal. Chem.*, 60:2299-2301 (1988)) and electrospray ionization (ESI) (Fenn et al., *Science*, 246:64-71 (1989); Yamashita et al., *J. Phys. Chem.*, 88:4451-4459 (1984)) has significantly increased the sensitivity of mass spectrometry of oligosaccharides (Spengler et al., *Anal. Chem.*, 62:1731-1737 (1990); Stahl et al., *Anal. Chem.*, 63:1463-1466 (1991); Powell et al., *Rapid Commun. Mass Spectrom.*, 10:1027-1032 (1996); Harvey et al., *Org. Mass Spectrom.*, 29:753-766 (1994); Cancilla et al., *Anal. Chem.*, 70:663-672 (1998)). Collision-induced dissociation (CID) provides considerable structural information. For example, the CID of alkali metal-coordinated species provides information regarding branching and linkage (Dell et al., *Carbohydr. Res.*, 115:41-52 (1983); Aubagnac et al., *Org. Mass Spectrom.*, 18:361-364 (1983); Barofsky et al., *Int. J. Mass Spectrom. Ion Phys.*, 53:319-322 (1983); Burlingame et al., *Anal. Chem.*, 56:417R-467R (1984); Burlingame et al., *Anal. Chem.*, 58:165R-211R (1986); Carroll et al., *Anal. Chem.*, 65:1582-1587 (1993); Dell et al., *Mass Spectrom. Rev.*, 3:357-394 (1984); Domon et al., *Glycoconjugate J.*, 5:397-409 (1988); Angel et al., *Carbohydrate Research*, 221: 17-35 (1991); Dell et al., *Int. J. Mass Spectrom. Ion Phys.*, 46:415-420 (1983); Dell et al., *Carbohydr. Res.*, 120:95-111 (1983); Forsberg et al., *J. Biol. Chem.*, 257:3555-3563 (1982); König et al., *J. Am. Soc. Mass Spectrom.*, 9:1125-1134 (1998)). Stereochemical information is even obtained by coordinating the oligosaccharides to transition metals followed by ESI and CID (König et al., id). However, structure determination using CID requires multiple rounds of tandem MS in order to obtain the complete oligosaccharide sequence. CID of oligosaccharides with pyranose reducing ends also produces the indiscriminate loss of fucose, a common terminating residue, thus masking its position in the chain (Cancilla et al., *J. Am. Chem. Soc.*, 118:6736-6745 (1996); Penn et al., *Anal. Chem.*, 68:2331-2339 (1996)). In addition, the loss of internal saccharide residues through intramolecular rearrangements are encountered with CID (Brüll et al., *J. Am. Soc. Mass Spectrom.*, 8:43-49 (1997)).

The present invention overcomes such limitations by using IRMPD to determine the structure of oligosaccharides. The use of IRMPD is advantageous because the representative fragmentation of oligosaccharides can be obtained down to the last residue. As a result, the complete sequencing of even large oligosaccharides can be performed in a single experiment. Prior to IRMPD analysis, tandem mass spectrometry techniques such as MALDI-Fourier transform mass spectrometry (FTMS) are used to identify oligosaccharide species in a sample (see, Tseng et al., *Anal. Biochem.*, 250:18-28 (1997); Tseng et al., *Anal. Chem.*, 71:3747-3754 (1999)). In particular, the capability of FTMS to provide accurate mass measurements (i.e., <10 ppm routinely, <5 ppm with internal calibration) is critical for obtaining rudimentary oligosaccharide compositions. For example, an oligosaccharide with a quasimolecular ion at m/z 2201.819 has three possible compositions within a tolerance of ± 0.1 mass units. Only with a tolerance of 0.01 mass units is the correct composition of two fucoses (Fuc), four hexoses (Hex), and six N-acetylhexosamines (HexNAc) obtained. The use of MALDI-FTMS according to the methods of the present invention can provide the correct composition from a number of possible compositions. The ability to perform multiple stages of tandem MS on ions produced by MALDI is another important feature of the mass spectrometry methods of the present invention.

VII. EXAMPLES

The following examples are offered to illustrate, but not to limit, the claimed invention.

Example 1

Analysis of Ovarian Cancer Cell Line Supernatant

This example illustrates the extraction and mass spectrometry analysis of O-linked oligosaccharides from the supernatant of four ovarian cancer cell lines.

Figure 3:
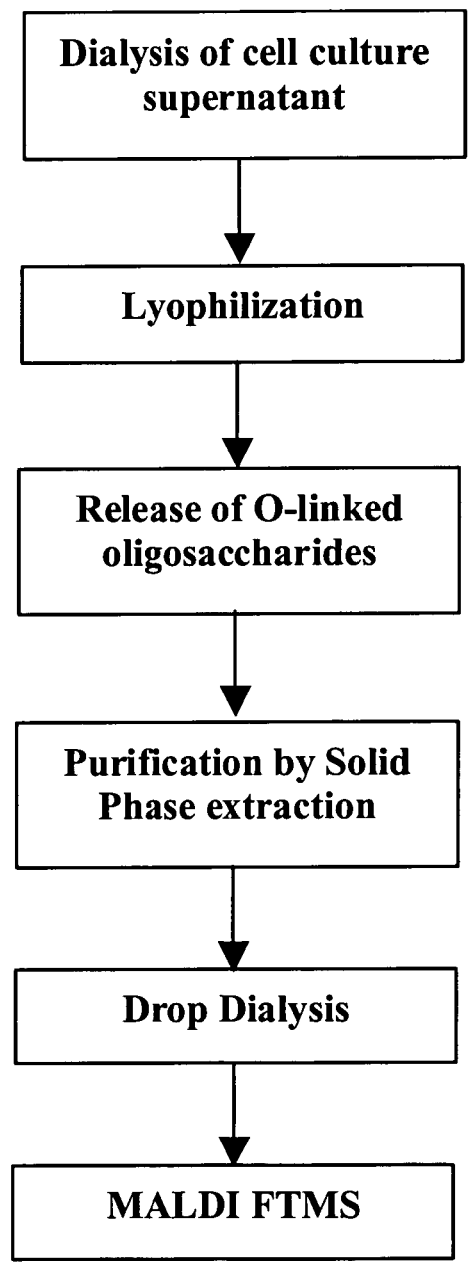
FIG. 3 shows a flowchart outlining the procedure for the selective release and isolation of O-linked oligosaccharides for MALDI-FTMS.

The procedure for the release and isolation of O-linked oligosaccharides is shown in FIG. 3. It is relatively fast and requires no HPLC separation. In fact, the entire procedure, from the extraction of O-linked oligosaccharides to mass spectrometry analysis, can be performed in less than 12 hours. The pre-concentration of the oligosaccharide components is performed with solid phase extraction and the analysis of entire mixtures is performed using mass spectrometry without any additional purification. The procedure requires only 1.0 µl of cell supernatant (equivalent to 2 µg of lyophilized starting material) to obtain a comprehensive O-linked oligosaccharide profile.

Dialysis is performed on the supernatant to remove most of the salts and small molecules. What remains are all of the large proteins, including all those that are glycosylated. Sodium tetrahydroborate ($NaBH_4$) under optimized conditions releases primarily O-linked oligosaccharides (Morelle et al., *Eur. J. Biochemistry*, 252:253-260 (1998)). As such, the release of N-linked oligosaccharides is minimized by selecting proper release conditions (e.g., temperature and time) for only the O-linked oligosaccharides. Indeed, careful inspection of the mass spectrum for samples prepared according to the above-described procedure reveals the absence of N-linked oligosaccharides, which are readily identified by their larger size and the presence of a specific core. Concentration of the oligosaccharide components is performed with porous graphitic carbon (PGC) solid phase extraction devices. These cartridges readily bind both neutral and anionic oligosaccharides. Salts are easily passed through while peptides and proteins are retained. By using the proper combination of elution solvents, neutral oligosaccharides are released separately from the anionic components.

Four ovarian cancer cell lines in both log and dead phases were examined (Table 1). Ovarian cancer cell lines were grown in indicated cell media supplemented with 10% fetal bovine serum, 100 units/ml penicillin/streptomycin, and 1% glutamine. ES-2 and SKOV-3 cells were grown in McCoy's media, while OVCAR-3 and CaOV-3 cells were grown in RPMI 1640 media. Conditioned media (CM) was removed from the cells during the log (non-confluent) or death (confluent) phase of cell growth and frozen at −70° C. The CM was thawed, sterile filtered (0.2 μm filter), and concentrated using Vivacell 70 or Vivaspin 20 concentrators (VivaScience). Alternatively, the filtered CM was dialyzed extensively against distilled water and then lyophilized. The resulting solution was then treated with the procedure shown in FIG. 3. To minimize the analysis time, there was no attempt to separate the oligosaccharide components. The cell culture supernatant was dialyzed (10 k MW cutoff) against nanopure water to remove salts and small molecules. The resulting solution contained only large proteins, including mucins. The solution was then lyophilized and treated with $NaBH_4$ and NaOH for 6 hours at 42° C. Under these conditions, only O-linked oligosaccharides were released. The sample was passed through a solid phase extraction cartridge with PGC to release the borate and sodium ions and isolate the oligosaccharide components. Oligosaccharides were released under three eluant ratios of acetonitrile and water. Three fractions were obtained with an increasing percentage of acetonitrile in water, i.e., 10%, 20%, and 40%. As controls, blank cultures and pure fetal bovine serum (FBS) were treated according to procedure shown in FIG. 3. Both control samples yielded a small number of oligosaccharides (<10) that was two orders of magnitude less than the number of oligosaccharides in the test samples. In addition, none of the oligosaccharides in the control samples was observed in the test samples.

TABLE 1

Ovarian cancer cell lines.

| Cell Line | Media | Phases |
| --- | --- | --- |
| CaOV-3 | RPMI 1640 | Log, Dead |
| OVCAR-3 | RPMI 1640 | Log, Dead |
| ES2 | McCoy's | Log, Dead |
| SK-OV-3 | McCoy's | Log, Dead |

Figure 4:
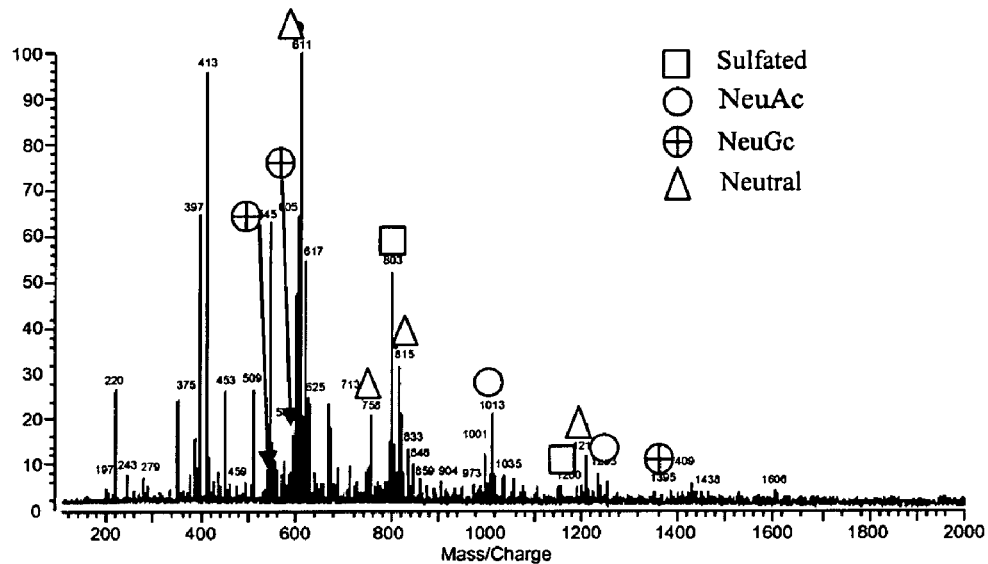
FIG. 4 shows the positive (A) and negative (B) MALDI-FTMS mass spectrum of the O-linked oligosaccharides from OVCAR-3 eluted by 10% acetonitrile.
Figure 4:
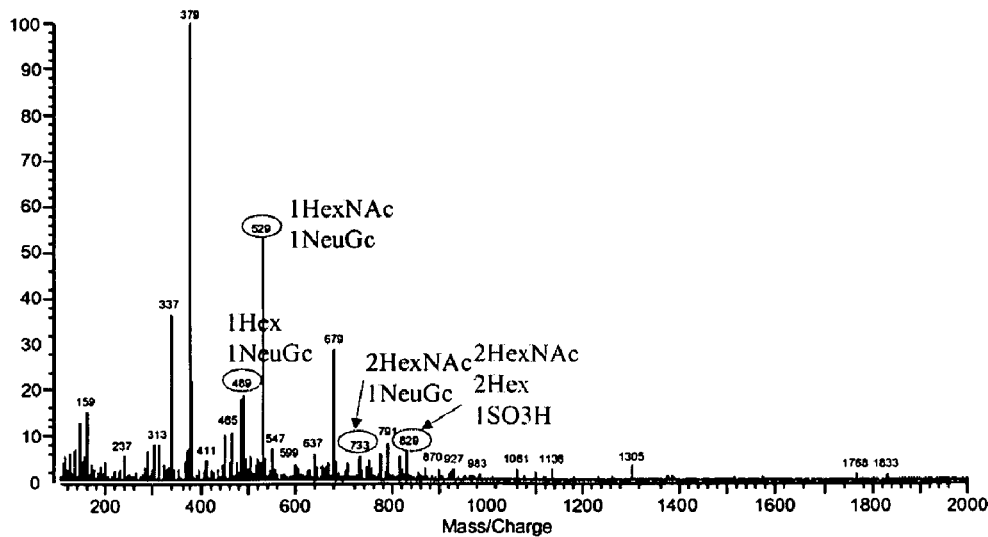

Each acetonitrile fraction contained a different oligosaccharide profile. For example, the 10% acetonitrile fraction contained mostly small, anionic, sialylated O-linked oligosaccharides for all four ovarian cancer cell cultures. FIG. 4 shows the positive ion (FIG. 4A) mass spectrum and the negative ion (FIG. 4B) mass spectrum of a sample from the CM of OVCAR-3 released from the PGC cartridge with 10% acetonitrile solution. Both spectra showed small, anionic O-linked oligosaccharides. The positive spectrum showed more chemical noise, while the negative spectrum showed these ions more clearly. Two types of sialylated O-linked oligosaccharides were observed: (1) N-acetylneuraminic acid (NeuAc)-containing O-linked oligosaccharides and (2) N-glycolylneuraminic acid (NeuGc)-containing O-linked oligosaccharides. In addition, a number of notable O-linked oligosaccharides were present, including two disaccharides with compositions of 1Hex:1NeuGc (m/z 488.169) and 1HexNAc:1NeuGc (m/z 529.122). As the presence of small anionic oligosaccharides indicates aberrations in the glycosylation of proteins, these oligosaccharides can be used as markers for the detection of adenocarcinomas such as ovarian cancer.

Figure 5:
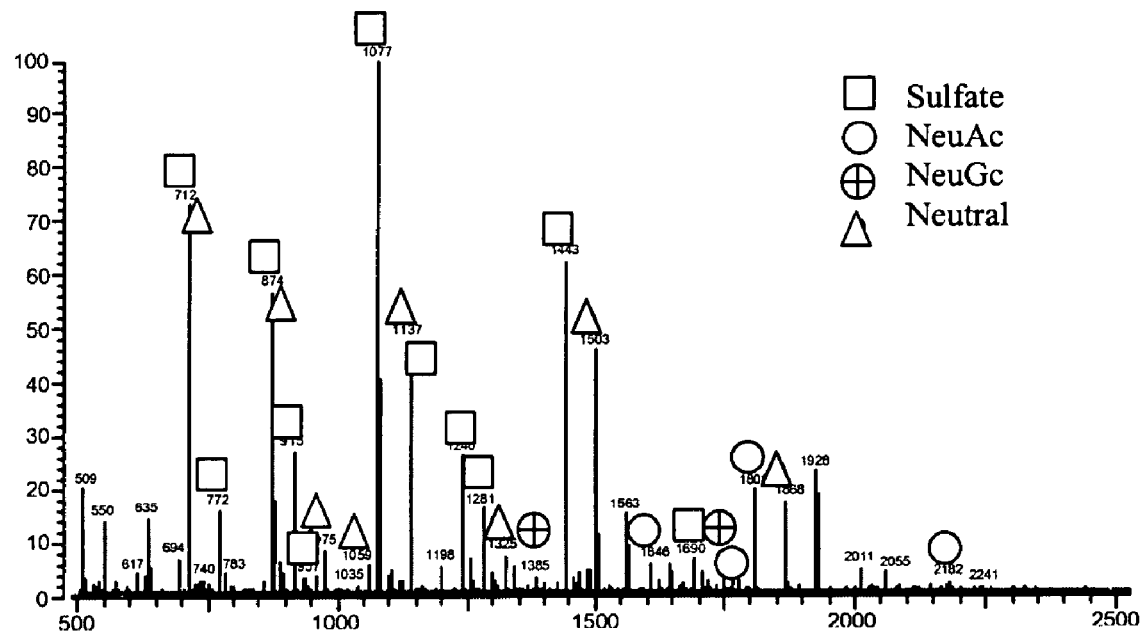
FIG. 5 shows the positive MALDI-FTMS mass spectrum of the O-linked oligosaccharides from OVCAR-3 eluted by 40% acetonitrile.

The 40% acetonitrile fraction contained significantly more and larger oligosaccharides. FIG. 5 shows the positive ion mass spectrum of a sample from the CM of OVCAR-3 released from the PGC cartridge with 40% acetonitrile solution. Nearly all of the signals detected in the 40% acetonitrile fraction corresponded to oligosaccharides. The spectrum showed neutral, sulfated, and sialylated (i.e., NeuAc and NeuGc) O-linked oligosaccharides. The largest oligosaccharides observed were around m/z 2200, corresponding to a 10-12-mer, significantly smaller than the 20-mers typically observed for normal cells. The 20% fraction also contained oligosaccharides, although nearly all of the oligosaccharides in the sample were found in the 10% and 40% acetonitrile fractions.

The high mass accuracy of Fourier transform ion cyclotron resonance mass spectrometry (FT-ICR-MS) is often sufficient to identify oligosaccharide peaks, even in complex mass spectra. To confirm the composition and to obtain sequence information, some of the ions from the acetonitrile fractions were isolated and subjected to tandem MS. To obtain fragmentation, infrared multiphoton dissociation (IRMPD) was used rather than collision-induced dissociation (CID). IRMPD has several advantages: (1) it does not require collision gas, thereby increasing repetition rate and the number of scans per spectra; and (2) fragments remain in the degradative beam, yielding often the complete sequence down to the last residue in a single tandem MS ($MS^2$) experiment. Standard CID experiments often require to $MS^3$ and even $MS^4$ to obtain the last residue in the sequence.

Figure 6:
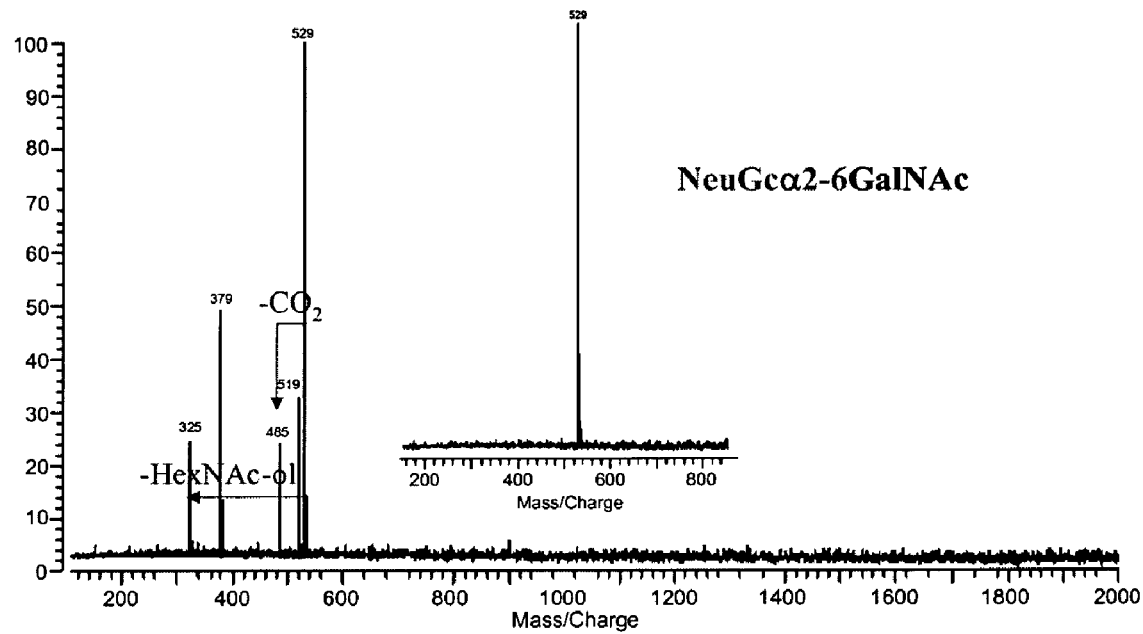
FIG. 6 shows the MALDI-FTMS mass spectrum (inset) and the IRMPD spectrum of an ionic species containing NeuGc with a composition corresponding to 1HexNAc:1NeuGc (m/z 529.122).

Several of the small, anionic oligosaccharide species were evaluated using IRMPD. For example, FIG. 6 shows the mass spectrum of an ionic species containing NeuGc with a composition corresponding to 1HexNAc:1NeuGc (m/z 529.122) that was isolated and subjected to IRMPD. Analysis of the ion m/z 529.122 in the negative mode using IRMPD yielded a spectrum wherein a loss of $CO_2$ was observed, consistent with the presence of carboxylic acid. The loss of a HexNAc-ol indicated that the reducing end corresponded to a HexNAc residue, while the remaining mass, m/z 325, corresponded to NeuGc. As a result, IRMPD analysis revealed that the structure of the 1HexNAc:1NeuGc (m/z 529.122) ionic species was NeuGcα2-6GalNAc. This structure can be verified by exoglycosidase digestion (see, e.g., Xie et al., *J. Am. Soc. Mass Spetrom.*, 12:877-884 (2001)). As such, with the methods of the present invention, small O-linked oligosaccharides are readily detected and NeuGc-containing oligosaccharides are readily detected and accurately identified.

Figure 7:
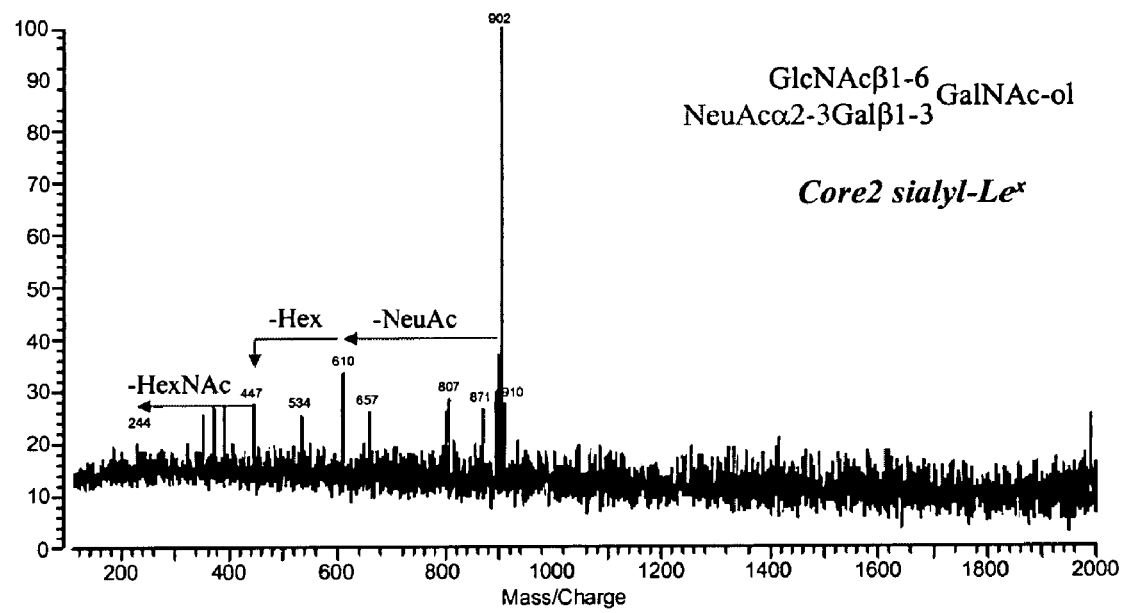
FIG. 7 shows the IRMPD spectrum of the NeuAc-containing ion m/z 902.322.

Oligosaccharides containing NeuAc were also observed. For example, FIG. 7 shows the mass spectrum of the NeuAc-containing ion m/z 902.322 that was isolated and subjected to IRMPD. This ion was not strongly abundant; however, the mass corresponded with the tetrasaccharide with the sialyl-$Le^x$ antigen. Analysis of the ion in the positive mode using IRMPD yielded a spectrum wherein the loss of a NeuAc (m/z 610), followed by a Hex (m/z 447), followed by the loss of a HexNAc (m/z 244) residue was observed. The reducing end in the alditol form was a HexNAc such as GalNAc. As a result, IRMPD analysis revealed that the structure of the m/z 902.322 ionic species was GlcNacβ1-6(NeuAcα2-3Galβ1-3)GalNAc. This structure can be confirmed by exoglycosidase digestion.

Figure 8:
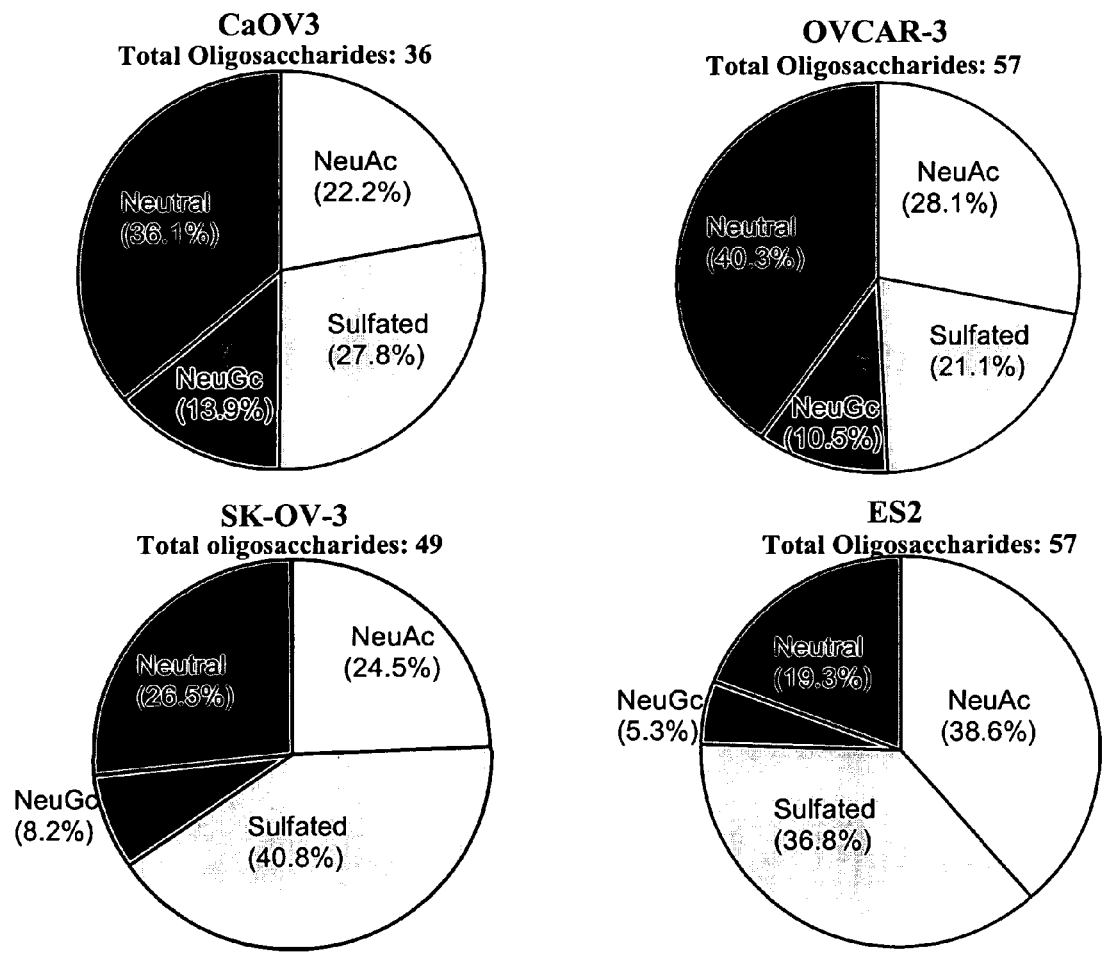
FIG. 8 shows the distribution of neutral, sulfated, NeuAc, and NeuGc O-linked oligosaccharides for the four ovarian cancer cell lines.

A summary of the O-linked oligosaccharides derived from OVCAR-3 cells is shown in Table 2. Similar mass spectra and compositions of O-linked oligosaccharides were obtained from the other three cell lines. FIG. 8 shows the distribution of neutral, sulfated, NeuAc, and NeuGc O-linked oligosaccharides for the four ovarian cancer cell lines. For example, at least 57 distinct masses were observed from the CM of OVCAR-3 cells.

TABLE 2

Oligosaccharide compositions identified in OVCAR-3 cells by MALDI-FTMS.

| HexNAc | Hex | NeuAc | NeuGc | Fuc | —SO₃H | MW | R.I. |
|---|---|---|---|---|---|---|---|
| 1 | 1 | | | | | 514.201 | W |
| 2 | 1 | | | | | 717.280 | M |
| 1 | 1 | 1 | | 2 | | 968.370 | M |
| 1 | 1 | 1 | | 3 | | 1114.427 | S |
| 2 | 1 | 1 | | 3 | | 1155.454 | S |
| 2 | 2 | 1 | | 1 | | 1187.444 | M |
| 3 | | 1 | | 2 | | 1212.476 | W |
| 2 | 3 | 1 | | 1 | | 1349.497 | S |
| | 4 | 1 | | 3 | | 1397.506 | W |
| 2 | 4 | 1 | | 1 | | 1511.549 | S |
| 1 | 4 | 1 | | 3 | | 1600.586 | W |
| 6 | 1 | 1 | | | | 1691.651 | S |
| 3 | 3 | 2 | | | | 1697.614 | M |
| 3 | 5 | 1 | | | | 1730.624 | W |
| 1 | 5 | 1 | | | | 1762.639 | M |
| 5 | 5 | 1 | | | | 2136.783 | M |
| | 1 | | 1 | | | 489.169 | S |
| 1 | | | 1 | | | 530.196 | S |
| 2 | | | 1 | | | 733.275 | M |
| | 1 | | 2 | | | 796.260 | M |
| | 4 | | 1 | | | 975.328 | S |
| 2 | 2 | | 1 | | | 1057.381 | M |
| | 5 | | 1 | | | 1137.380 | M |
| 1 | 5 | | 1 | | | 1340.460 | W |
| 2 | 3 | 1 | | 2 | | 1511.549 | S |
| 2 | 1 | | | | 1 | 668.195 | S |
| 2 | 2 | | | | 1 | 830.247 | S |
| 3 | 1 | | | | 1 | 871.274 | S |
| 4 | | | | | 1 | 912.301 | M |
| 3 | 2 | | | | 1 | 1033.327 | S |
| 3 | 3 | | | | 1 | 1197.380 | S |
| 4 | 2 | | | | 1 | 1236.406 | W |
| 4 | 4 | | | | 1 | 1560.512 | W |
| 2 | 1 | | | | | 588.238 | S |
| 2 | 1 | | | 1 | | 734.296 | S |
| 2 | 2 | | | | | 750.291 | S |
| 3 | 1 | | | | | 791.317 | S |
| 4 | | | | | | 832.344 | M |
| 3 | 2 | | | | | 953.370 | M |
| 5 | | | | | | 1035.423 | M |
| 3 | 3 | | | | | 1115.423 | S |
| 2 | 2 | | | 3 | | 1188.464 | M |
| 2 | 3 | | | 2 | | 1204.459 | S |
| 1 | 3 | | | 4 | | 1293.496 | S |
| 4 | 2 | | | 1 | | 1302.507 | M |
| 4 | 3 | | | | | 1318.502 | M |
| 2 | 3 | | | 3 | | 1350.517 | M |
| 4 | 4 | | | | | 1480.555 | M |
| 5 | 1 | | | 2 | | 1489.592 | M |
| 4 | 1 | | | 4 | | 1578.628 | S |
| 5 | 3 | | | 1 | | 1667.639 | M |
| 4 | 2 | | | 4 | | 1740.681 | S |

Compositions were determined by exact mass analyses in both positive and negative mode.
R.I. = Relative Intensity.
S = strong;
M = moderate;
W = weak.

A number of conclusions can be drawn from the analysis of the four cancer cell lines: (1) the oligosaccharides obtained are small and correspond to O-linked species from glycoproteins such as mucins; (2) oligosaccharides known to be present in cancer cells are represented; and (3) there are many common oligosaccharides between the four cell lines, but there are also distinct oligosaccharides specific to each cell line.

Example 2

Analysis of Cancer Patient Serum

This example illustrates the extraction and mass spectrometry analysis of O-linked oligosaccharides from the serum of a patient with ovarian cancer.

Serum from a patient with very high CA 125 levels (11621 units/ml) was examined by employing the procedure described in FIG. 3. Serum was isolated from whole blood using standard clinical procedures. The serum was tested for CA 125 using the AXSYM test for CA 125(Abbott). After testing, the serum (1.5 ml) was dialyzed extensively against nanopure water and lyophilized, yielding 20 mg of powder. A fraction (2 mg) was treated with NaBH₄ and NaOH, processed, and analyzed by mass spectrometry as described above for cell supernatants.

Figure 9:
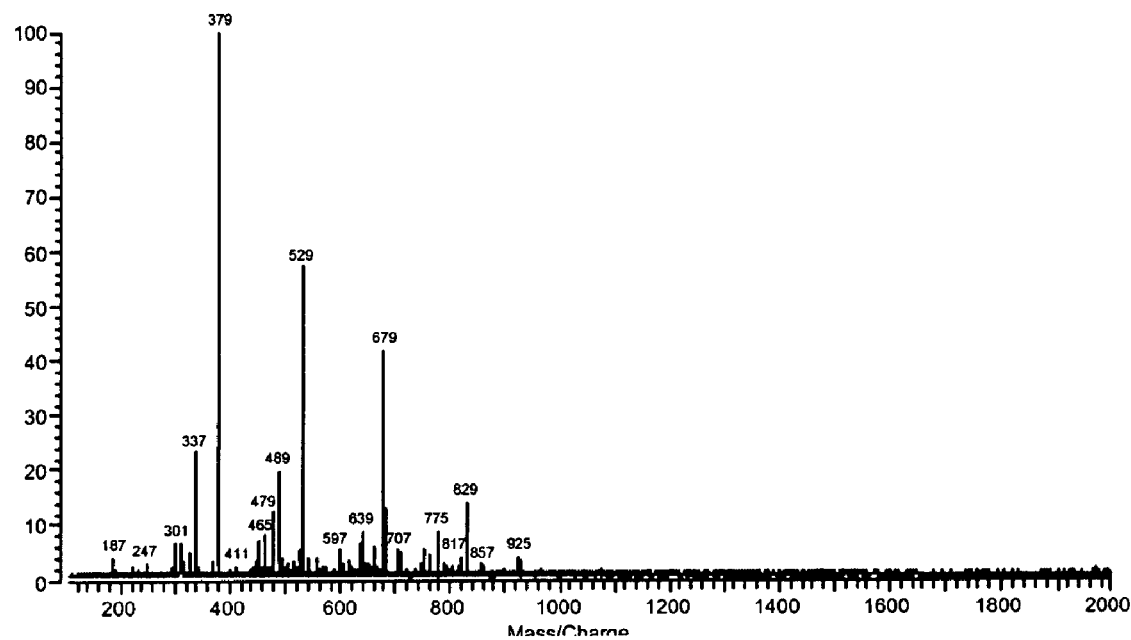
FIG. 9 shows a negative MALDI-FTMS mass spectrum of the O-linked oligosaccharides from the serum of a patient with ovarian cancer eluted by 20% acetonitrile.
Figure 10:
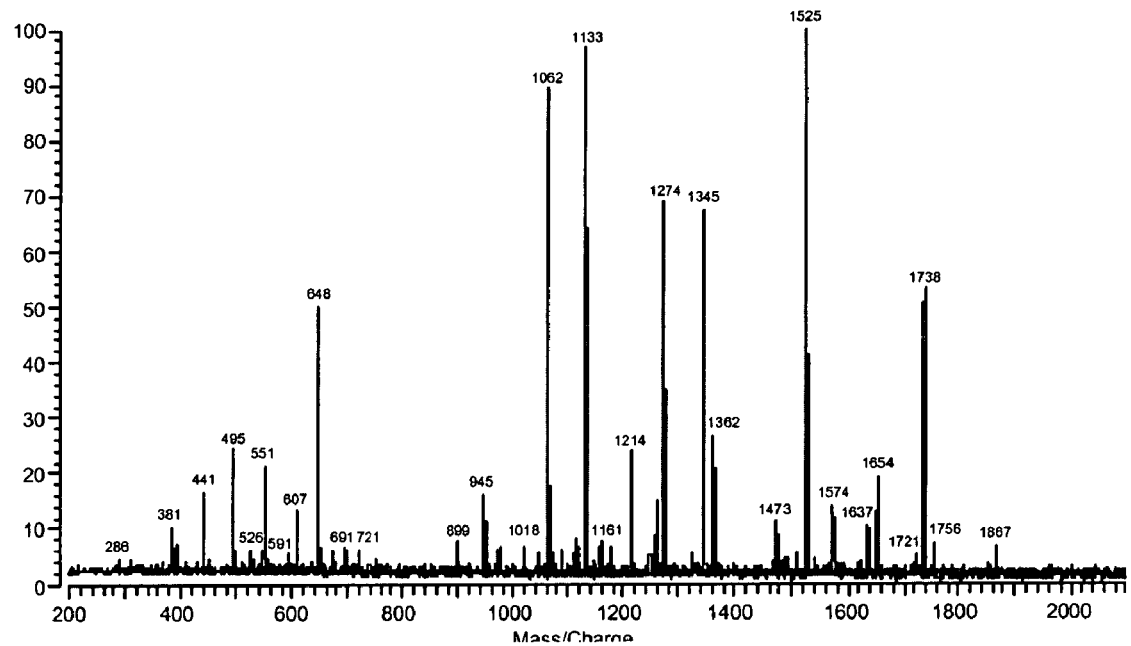
FIG. 10 shows a positive MALDI-FTMS mass spectrum of the O-linked oligosaccharides from the serum of a patient with ovarian cancer eluted by 40% acetonitrile.

FIG. 9 shows a negative mass spectrum of the fraction eluted by 20% acetonitrile from the PGC cartridge. FIG. 10 shows a positive mass spectrum of the fraction eluted by 40% acetonitrile from the PGC cartridge. Although both mass spectra contained anionic oligosaccharides, small anionic oligosaccharides were observed in the fraction eluted by 20% acetonitrile, while larger anionic oligosaccharides were observed in the fraction eluted by 40% acetonitrile. The small anionic oligosaccharides are particularly useful as markers for diagnosing adenocarcinomas such as ovarian cancer, while the larger anionic oligosaccharides are particularly useful as markers for differentiating between adenocarcinomas such as ovarian cancer and breast cancer.

A summary of the O-linked oligosaccharides derived from the serum sample is shown in Table 3. Each peak in the mass spectra was confirmed as representing an oligosaccharide based on the exact mass. In addition, about 10 of the peaks were confirmed by tandem MS. As shown in Table 3, five NeuGc-containing oligosaccharides and eight NeuAc-containing oligosaccharides were present in the comprehensive O-linked oligosaccharide profile of a patient with very high CA 125 levels. Small sialylated oligosaccharide with compositions such as 1NeuAc:1HexNAc, 1NeuGc:1Hex, 1NeuGc: 1Hex NAc, and 1NeuGc:1Hex:2HexNAc were identified in this group of oligosaccharides. As the presence of small anionic oligosaccharides indicates aberrations in the glycosylation of proteins, such small sialylated oligosaccharides can be used as markers for the detection of adenocarcinomas such as ovarian cancer.

TABLE 3

Oligosaccharide compositions identified in cancer patient serum by MALDI-FTMS.

| HexNAc | Hex | NeuAc | NeuGc | Fuc | —SO₃H | MW | RI |
|---|---|---|---|---|---|---|---|
| 1 | | 1 | | | | 514.201 | M |
| | 1 | | | 2 | | 603.237 | S |
| | 1 | 1 | 1 | | | 618.212 | M |
| 3 | 1 | 1 | | 1 | | 1228.470 | S |
| 6 | | 1 | | | | 1529.598 | M |
| 4 | 2 | 1 | | 1 | | 1593.603 | M |
| 4 | 3 | 1 | | | | 1609.598 | M |
| 6 | 1 | 1 | | | | 1691.651 | S |
| | 1 | | 1 | | | 489.169 | M |
| 1 | | | 1 | | | 530.196 | S |
| 1 | 2 | | 1 | | | 854.301 | W |

TABLE 3-continued

Oligosaccharide compositions identified in cancer patient serum by MALDI-FTMS.

| HexNAc | Hex | NeuAc | NeuGc | Fuc | —SO$_3$H | MW | RI |
|---|---|---|---|---|---|---|---|
| 2 | 1 |  | 1 | 3 |  | 1333.502 | M |
| 1 |  |  |  | 1 | 1 | 449.120 | M |
| 1 | 1 |  |  |  | 1 | 465.115 | M |
| 2 |  |  |  |  | 1 | 506.142 | M |
| 2 | 2 |  |  |  | 1 | 830.247 | M |
| 1 | 1 |  |  | 3 | 1 | 903.289 | S |
| 3 | 1 |  |  | 1 | 1 | 1017.332 | S |
| 5 |  |  |  |  | 1 | 1115.380 | W |
| 2 | 4 |  |  | 1 | 1 | 1300.411 | S |
| 2 | 5 |  |  |  | 1 | 1316.406 | S |
| 6 | 1 |  |  |  | 1 | 1480.512 | S |
| 2 | 4 |  |  | 3 | 1 | 1592.527 | S |
| 2 | 5 |  |  | 2 | 1 | 1608.522 | S |
| 4 | 2 |  |  | 4 | 1 | 1820.638 | W |
| 5 | 4 |  |  | 2 | 1 | 2055.707 | M |
| 1 | 8 |  |  | 4 | 1 | 2183.716 | M |
| 3 |  |  |  | 2 |  | 921.380 | M |
| 4 | 1 |  |  |  |  | 994.397 | M |
| 1 | 4 |  | 1 |  |  | 1017.375 | M |
| 1 | 2 |  |  | 4 |  | 1131.443 | M |
| 2 | 3 |  |  | 3 |  | 1350.517 | M |
| 3 | 5 |  |  | 2 |  | 1731.644 | M |
| 7 |  |  |  | 2 |  | 1733.698 | M |
| 5 | 2 |  |  | 4 |  | 1943.760 | M |

Compositions were determined by exact mass analyses in both positive and negative mode.
R.I. = Relative Intensity.
S = strong;
M = moderate;
W = weak.

To confirm the assignment of ions identified by MALDI-FTMS and to obtain structural information, some of the ions were isolated and further analyzed using IRMPD. For example, the spectrum of ion m/z 529 was isolated and subjected to IRMPD analysis. The spectrum for this ion was identical to the ion of the same mass from the ovarian cancer cell line OVCAR-3 (see, FIG. 6). As a result, the presence of NeuGc in the serum of a patient with ovarian cancer was confirmed. The structure of this ionic species can be verified by exoglycosidase digestion. As such, with the methods of the present invention, small O-linked oligosaccharides are readily detected in serum samples and NeuGc-containing oligosaccharides are readily detected and accurately identified in serum samples.

Example 3

Identification of Oligosaccharide Markers in Ovarian Cancer Cell Lines

This example illustrates the determination and comparison of oligosaccharides found in the ovarian cancer cell lines shown in Table 1.

Oligosaccharides isolated from each of the ovarian cancer cell lines are classified as neutral, sialylated (e.g., NeuAc and NeuGc), or sulfated. In addition, oligosaccharides that are common and those that are unique to each of the cell lines are determined. The structures of individual oligosaccharides can also be elucidated (see, Example 4, below). The identified oligosaccharides are then compared to those obtained from the serum of individuals with and without cancer. Furthermore, a database of the oligosaccharides identified from the four cancer cell lines under various nutrient and medium conditions can be constructed. For comparison, the conditioned medium of human cells obtained from normal tissues such as breast, ovary, liver, colon, and lung can be examined. Such comparisons between the oligosaccharides identified from normal tissues and those identified from a cancer cell line can be used to elucidate oligosaccharide markers specific to the cancer cell line.

The ratio of NeuGc-containing oligosaccharides to NeuAc-containing oligosaccharides can also be determined for each cancer cell line and compared to the ratio found in normal tissue. In certain instances, a higher ratio is present in the cancer cell line as compared to normal tissue. In addition, the amount of sulfated oligosaccharides between a cancer cell line and normal tissue can be compared. In certain instances, a lower percentage of sulfated oligosaccharides is present in the cancer cell line as compared to normal tissue.

Figure 11:
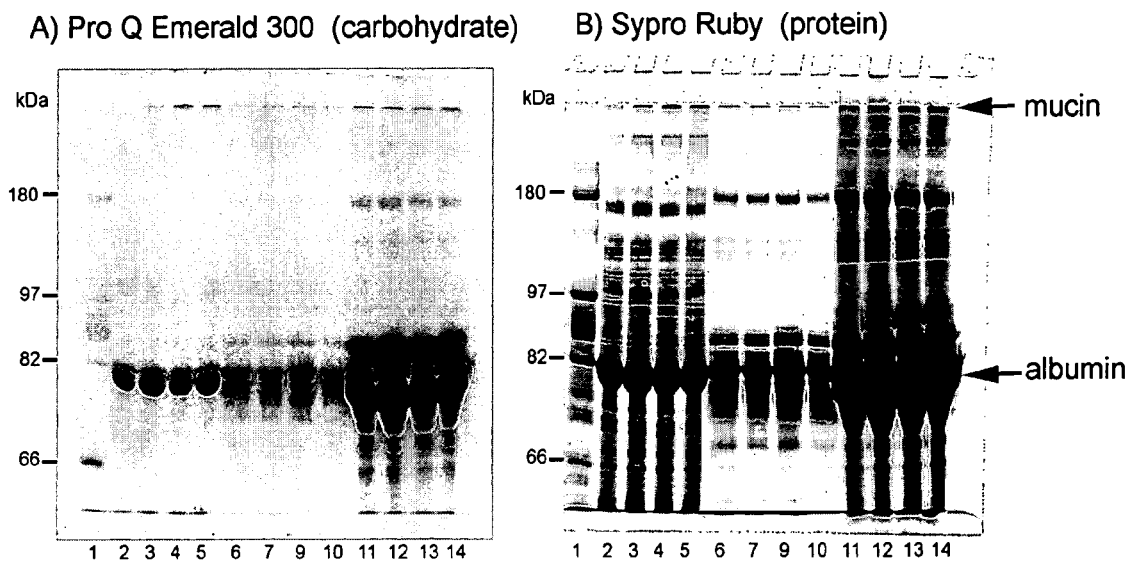
FIG. 11 shows the results of a 1-D gel separation of proteins from each of the four ovarian cancer cell lines stained with Pro Q Emerald 300 (A) or Sypro Ruby (B).

To confirm that O-linked oligosaccharides from mucins are released and isolated, 1-D gel separation of the proteins in the cell supernatant or conditioned medium from a cancer cell line or from human serum can be performed. FIG. 11 shows the results of a 1-D gel separation of proteins from each of the four ovarian cancer cell lines stained with Pro Q Emerald 300 (Molecular Probes) (FIG. 11A) or Sypro Ruby (Molecular Probes) (FIG. 11B). More particularly, conditioned media (CM) from ovarian cancer cell lines ES-2 (lanes 2, 6, 11), SKOV-3 (lanes 3, 7, 12), CaOV-3 (lanes 4, 8, 13), and OVCAR-3 (lanes 5, 9, 14) were concentrated, subjected to depletion of albumin through the use of Cibracron blue agarose (Sigma), and then resolved by SDS-PAGE (7.5%). Lane 1: molecular weight markers; Lanes 2-5: samples after treatment with Cibracron Blue; Lanes 6-9: samples of proteins solubilized in urea/CHAPS buffer; Lanes 10-13: proteins bound and eluted from Cibracron blue agarose with SDS-PAGE sample buffer. The gels illustrate the complexity of the protein mixture from conditioned medium. Albumin is the most abundant species and typically saturates most methods of detection. However, in this instance, most of the albumin has been removed. In addition, the mucin glycoproteins are clearly separated from other proteins as indicated by the carbohydrate stain (FIG. 11A). The glycoproteins on the gel can be collected and the oligosaccharides released to confirm that the oligosaccharides obtained from conditioned medium represent mucin oligosaccharides.

To determine whether NeuGc-containing oligosaccharides arise from an endogenous source (e.g., the cells themselves) or from an exogenous source (e.g., the conditioned medium), the cancer cell lines were cultured in media without fetal bovine serum (FBS) to eliminate the endogenous source of NeuGc-containing oligosaccharides. Alternatively, the cancer cells can be cultured in serum-free media after the cells have been washed free of any FBS. Cells can be cultured in FBS-free media over several generations, and in each generation, the amount of NeuGc-containing oligosaccharides can be monitored relative to other oligosaccharides such as NeuAc-containing oligosaccharides. If the amount of NeuGc-containing oligosaccharides decreases in every generation, then these oligosaccharides are likely from an exogenous source. Such studies can also be performed on human serum samples.

Table 4 shows the oligosaccharide species isolated from a 40% acetonitrile eluant of ES2 cells cultured either in FBS or FBS-free media. The results indicate that NeuGc-containing oligosaccharides are present in both samples. Since the cells cultured in FBS-free medium were obtained from a serum nutrient sample, the nutrient sample itself can be examined for the presence of residual NeuGc-containing oligosaccharides.

TABLE 4

Oligosaccharide species present in the conditioned media of ES-2 cells cultured in FBS or FBS-free serum.

| Oligosaccharide Species (Composition) | FBS | FBS-Free |
|---|---|---|
| 1 HexNAc 1 Hex 1 Sulf | | x |
| 1 HexNAc 1 NeuAc | x | x |
| 1 HexNAc 1 NeuGc | | x |
| 1 HexNAc 1 Hex 1 Fuc | x | |
| 1 HexNAc 1 NeuAc 1 Fuc | | x |
| 1 HexNAc 1 Hex 1 NeuAc | x | x |
| 1 HexNAc 1 Hex 1 NeuGc | x | x |
| 1 HexNAc 3 Hex | x | x |
| 2 HexNAc 2 Hex | x | x |
| 2 HexNAc 2 Hex 1 Sulf | | x |
| 1 HexNAc 1 Hex 1 NeuGc 1 Fuc | x | x |
| 1 HexNAc 2 Hex 1 NeuAc | x | x |
| 1 HexNAc 2 Hex 1 NeuGc | | x |
| 1 HexNAc 2 NeuAc 1 Fuc | x | |
| 1 HexNAc 4 Hex 1 Sulf | x | |
| 1 HexNAc 1 Hex 1 NeuAc 2 Fuc | | x |
| 2 HexNAc 3 Hex 1 Sulf | x | x |
| 2 HexNAc 2 NeuAc | | x |
| 3 HexNAc 1 Hex 1 NeuGc | x | x |
| 3 HexNAc 3 Hex 1 Sulf | x | x |
| 2 HexNAc 4 Hex 1 Fuc 1 Sulf | | x |
| 2 HexNAc 2 Hex 1 NeuAc 2 Fuc | | x |
| 3 HexNAc 1 Hex 2 NeuAc | x | x |
| 2 HexNAc 3 Hex 1 NeuAc 2 Fuc | | x |
| 2 HexNAc 4 Hex 1 NeuAc 1 Fuc | | x |
| 3 HexNAc 2 Hex 1 NeuGc 3 Fuc | x | |
| 3 HexNAc 3 Hex 1 NeuAc 2 Fuc | x | |

The number of sulfated oligosaccharides can also be determined for each of the cancer cell lines. For example, the OVCAR-3 cancer cell line contains at least 11 sulfated oligosaccharides, many in large abundance. FIG. 5 shows several of these sulfated oligosaccharide species, e.g., m/z 712.166, 874.219, 1077.298, and 1443.430. Sulfated oligosaccharides were observed in all four ovarian cancer cell lines tested.

Example 4

Oligosaccharide Structure Determination

This example illustrates the determination of rudimentary and fine structures of the O-linked oligosaccharides identified from ovarian cancer cell lines or patient serum.

The determination of the O-linked oligosaccharide structures is important for the identification of markers suitable for detecting or diagnosing cancers such as adenocarcinomas. As such, the present invention provides methods for O-linked oligosaccharide structure determination using tandem MS to obtain rudimentary structures followed by selective exoglycosidase digestion to verify those structures.

Exoglycosidases, e.g., in the form of glycosidase arrays, are commonly used for the structural elucidation of N-linked oligosaccharides. However, unlike N-linked oligosaccharides, where there is a known number of putative structures, O-linked oligosaccharides have significantly greater combinations of structures. As a result, the use of glycosidase arrays for determining the structures of O-linked oligosaccharides can be both expensive and time-consuming. The present invention overcomes such limitations through the targeted use of exoglycosidase digestion that takes advantage of rudimentary structures obtained from tandem MS experiments (e.g., collision-induced dissociation (CID) or IRMPD). Thus, the procedure for the complete structural elucidation of O-linked oligosaccharides involves the following steps. (1) obtain the exact mass to determine the general composition of the residues (e.g., N-acetylhexose (HexNAc), hexose (Hex), fucose (Fuc), N-acetylneuraminic acid (NeuAc), or N-glycolylneuraminic acid (NeuGc)); (2) determine the rudimentary structure using CID or IRMPD; (3) perform exoglycosidase digestion based upon the rudimentary structure to determine the identity of the residue, the linkage, and the anomeric character of the linkage.

Figure 12:
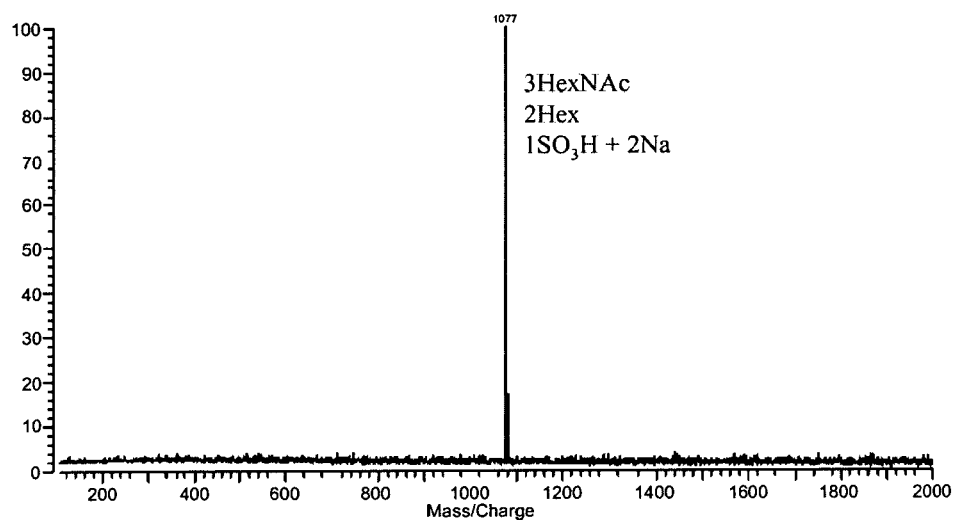
FIG. 12 shows the MALDI-FTMS mass spectrum (A) and the IRMPD spectrum (B) of a sulfated O-linked oligosaccharide isolated from CaOV-3.
Figure 12:
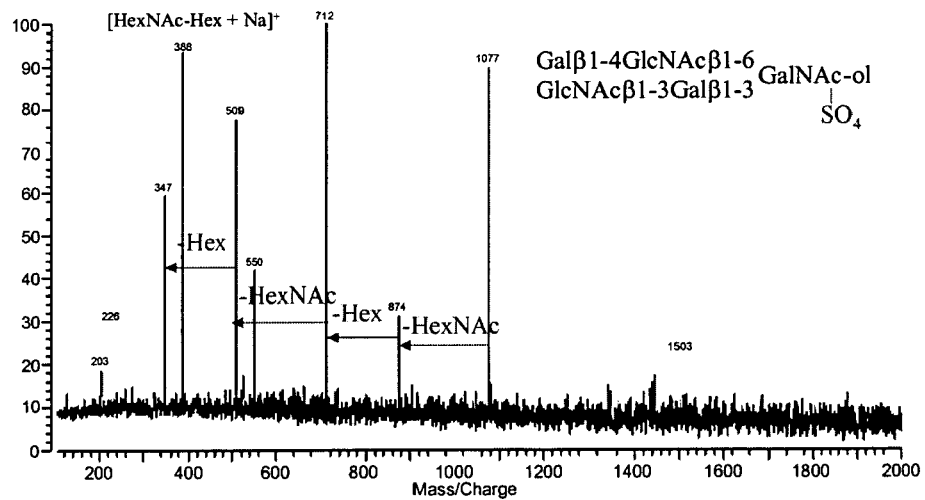

Preferably, O-linked oligosaccharide structures are determined using IRMPD. The use of IRMPD is advantageous because it does not require collision gas, thereby increasing repetition rate and the number of scans per spectra. Further, fragments remain in the degradative beam, often yielding the complete sequence down to the last residue. As a result, the complete sequencing of even large oligosaccharides can be performed in a single experiment. For example, FIG. 12 shows the IRMPD spectrum for a sulfate ester-containing oligosaccharide isolated from CaOV-3. Based on the exact mass of m/z 1077.298 (positive mode, theoretical mass 1077.290), the ion was identified as containing 3 HexNAc residues, 2 Hex residues, and one sulfate group (FIG. 12A). Isolation of the quasimolecular ion was then performed using standard FTMS techniques. Fragmentation of the isolated ion was performed by irradiating the ion for a period of 0.75 s with a laser power of 11 Watts (FIG. 12B). As shown in FIG. 12B, a number of product ions were formed, including m/z 347, which corresponded to a sulfated alditol HexNAc (i.e., GalNAc) residue. FIG. 12B also shows that, upon fragmentation, the quasimolecular ion alternated between loss of a HexNAc residue and a Hex residue. Further, the ion at m/z 388 was identified as a HexNAc-Hex fragment. Based upon these results and the known glycobiology of cancer, the structure for the oligosaccharide was then determined (FIG. 12B).

Oligosaccharide structures can be verified using exoglycosidase digestion. For example, an exoglycosidase specific to Gal(β1-4) can be used to determine whether the terminal galactose can be cleaved. Another exoglycosidase, N-acetylglucosaminidase, can then be used to determine the position and verify the identity of the GlcNAc residue. IRMPD can also be performed on the exoglycosidase products to verify the positions of the residues.

Example 5

Statistical Analyses of Oligosaccharide Markers

This example illustrates the use of statistical analyses to identify oligosaccharide markers while controlling for false positives and to classify and predict cancer based upon an oligosaccharide profile. Variations in oligosaccharide measurements from ovarian cell lines, human serum (e.g., normal, ovarian cancer, and breast cancer serum) are also quantified.

Statistical classification or prediction analysis of an oligosaccharide profile is similar to statistical analysis of genomic and proteomic data. As such, based upon the oligosaccharide marker profiles obtained from ovarian cancer cell lines and human serum, statistical classification/prediction analysis is performed to discriminate between normal and ovarian cancer samples. For example, to predict ovarian cancer samples with various (e.g., increasing) levels of CA 125, statistical learning methodologies such as dimension reduction combined with discriminant analysis (Nguyen et al., *Bioinformatics*, 18:39-50 (2002); Nguyen et al., *Bioinformatics*, 18:1216-1226 (2002)), support vector machine (Furey et al., *Bionformatics*, 16:906-914 (2000); Vapnik, *Statistical Learning Theory*, Wiley-Interscience: New York (1998)), and penalized discriminant analysis(Hastie et al., *The elements of statistical learning: Data mining, inference, and prediction*, Springer: New York, N.Y. (2001)) are implemented. Prediction models are constructed based upon a set of training samples. Model validation and error rates for ovarian cancer prediction based upon an oligosaccharide profile are obtained from an independent data set, consisting of samples not used in the model construction (Ambroise et al., *Proc. Natl. Acad. Sci. U.S.A.*, 99:6562-6566 (2002); Hand, *Construction and Assessment of Classification Rules*, John Wiley: Chichester, England (1997)).

In addition to using a set of oligosaccharide markers (e.g., approximately 50-70) for cancer prediction and classification analyses, statistical analyses can be performed based upon the complete oligosaccharide mass spectrum obtained for each sample. Statistical pattern recognition methods can then be used to identify profiles unique to cancer samples. For example, dimension reduction techniques such as partial least squares (Nguyen et al., *Bioinformatics*, 18:39-50 (2002); Nguyen et al., *Bioinformatics*, 18:1216-1226 (2002)) can be employed due to the large number of molecular species. This technique can also be used to identify a specific oligosaccharide marker or a combination of oligosaccharide markers that are predictive of a particular class of cancer. More particularly, statistical classification and prediction analyses can be used for distinguishing ovarian cancer serum from breast cancer serum.

Statistical analysis can also be used to compare the expression levels of oligosaccharides between different groups of samples, such as between non-disease and ovarian cancer serum, or between ovarian cancer serum with different levels of CA 125. For example, statistical methods that have been developed for genomic and proteomic data can be implemented (Efron et al., *J. Am. Stat. Assoc.*, 90:1151-1160 (2001)). Since the number of oligosaccharide markers being compared is relatively large, the false positive discovery rate can be controlled (Nguyen et al., *Bioinformatics*, 18:39-50 (2002); Nguyen et al., *Bioinformatics*, 18:1216-1226 (2002); Benjamini et al., *J. Royal Stat. Soc. B*, 57:289-300 (1995)). Such comparative statistical analyses with false positive discovery rate control can be based upon data obtained from a large number of replications. In addition to sampling replicates, data from technical replicates can be obtained by running multiple experiments using the same serum sample (i.e., from fixed individual), allowing quantification of the variability of the measurement process. Preferably, technical variability is low relative to sampling variability.

Example 6

Quantitative Measurement of Oligosaccharide Markers

This example illustrates methods for the quantitation of oligosaccharide markers in human serum using mass spectrometry.

In one method, several oligosaccharide species released from human serum are tracked simultaneously, with an oligosaccharide from a cancer cell line included as an internal calibrant. Oligosaccharides from that cell line are released with $NaBD_4$, resulting in the incorporation of a single deuterium in the alditol products. The calibrant oligosaccharides are one mass unit higher than the serum oligosaccharides and do not interfere with the analysis. As the calibrant contains all classes of O-linked oligosaccharides, e.g., neutral, sialylated (NeuAc and NeuGc), and sulfated oligosaccharides, the effect of suppression is minimized because both calibrant and analyte are suppressed equally. The deuterated standard oligosaccharide concentration can be determined using known standards for each class of oligosaccharide. The standard oligosaccharide solution form the cancer cell line is then added to the oligosaccharides released from the test serum sample.

In another method, commercially available internal standards such as small neutral, sialylated (NeuAc and NeuGc), and/or sulfated oligosaccharides are added to the oligosaccharides released from the test serum sample.

In yet another method, naturally-occurring internal standards, e.g., oligosaccharides that are present in the serum of only healthy individuals, are added to the oligosaccharides released from the test serum sample. The ratio of the oligosaccharides that are present in the serum of only healthy individuals to those that are expressed in the test serum sample can then be monitored and used as an indicator of the disease. For example, the ratio of NeuGc-containing oligosaccharides from the test serum sample to NeuAc-containing oligosaccharides from the serum of only healthy individuals can be monitored and used as an indicator of the disease.

Example 7

Identification of Oligosaccharide Markers from Breast Cancer Cells

This example illustrates methods for the identification of oligosaccharide markers specific to breast cancer.

Breast cancer and ovarian cancer share many biological features. For example, both types of cancer involve epithelial cells that secrete mucins. In addition, both types of cancer produce small anionic oligosaccharides. As a result, some or all of the oligosaccharide markers identified for ovarian cancer can be used as an indicator of breast cancer. Breast cancer cells can be examined for both unique oligosaccharides and those that are common between breast cancer and ovarian cancer. Breast cancer cell lines suitable for examination include, without limitation, MCF7, MDA-MB-231, MDA-MB-468, MDA-MB-361, MDA-MD-453, and BT-474 cell lines, obtained from ATCC. These cell lines can be propagated in DMEM, 10% FBS, 1% glutamine, 100 u/ml penicillin/streptomycin or in media recommended by ATCC at 37° C. with 5% $CO_2$. Cell lines can also be grown for 2-7 days in serum-free media after several rinses in serum-free media to remove any remaining fetal bovine serum (FBS). Conditioned media (CM) can be removed from the cells, sterile filtered (0.22 µ), and frozen. Samples are processed and the O-linked oligosaccharides released by β-elimination with basic $NaBH_4$ as described above. The resultant oligosaccharides are then analyzed by mass spectrometry.

The MCF7 cell line was originally isolated from a pleural effusion adenocarcinoma. The BT-474 was isolated from a solid, invasive ductal carcinoma of the breast. The MDA-MB-453 cell line was derived from an effusion from a cancer patient with metastatic carcinoma of the breast. The MDA-MB-361 cell line was isolated from a brain metastasis (adenocarcinoma) from a breast cancer patient. The MDA-MB-468 cell line was isolated from the pleural effusion of a female patient with metastatic adenocarcinoma of the breast. The MDA-MB-231 cell line was obtained from a pleural effusion adenocarcinoma of the mammary gland. The MCF-10F and MCF-10A cell lines can be used as the normal control. These cell lines were obtained from the mammary gland (breast) of patients with fibrocystic disease. These are non-tumorigenic epithelial cell lines that are positive for epithelial sialomucins. Alternatively, the conditioned medium from human cells derived from normal breast, commercially available from BioWhittaker Inc, can be used as the normal control. Oligosaccharide markers from these breast cancer cell lines can be identified and those specific to breast cancer and ovarian cancer can be determined. As such, a distinct set of oligosaccharide markers can be used to distinguish between breast cancer and ovarian cancer.

Example 8

Identification of Oligosaccharides from Human Serum

This example illustrates the identification of oligosaccharides from the serum of normal individuals and the serum from individuals with low CA 125 levels (Group I), high CA 125 levels (Groups II and III), and extremely high CA 125 levels (Lim 6).

Figure 13:
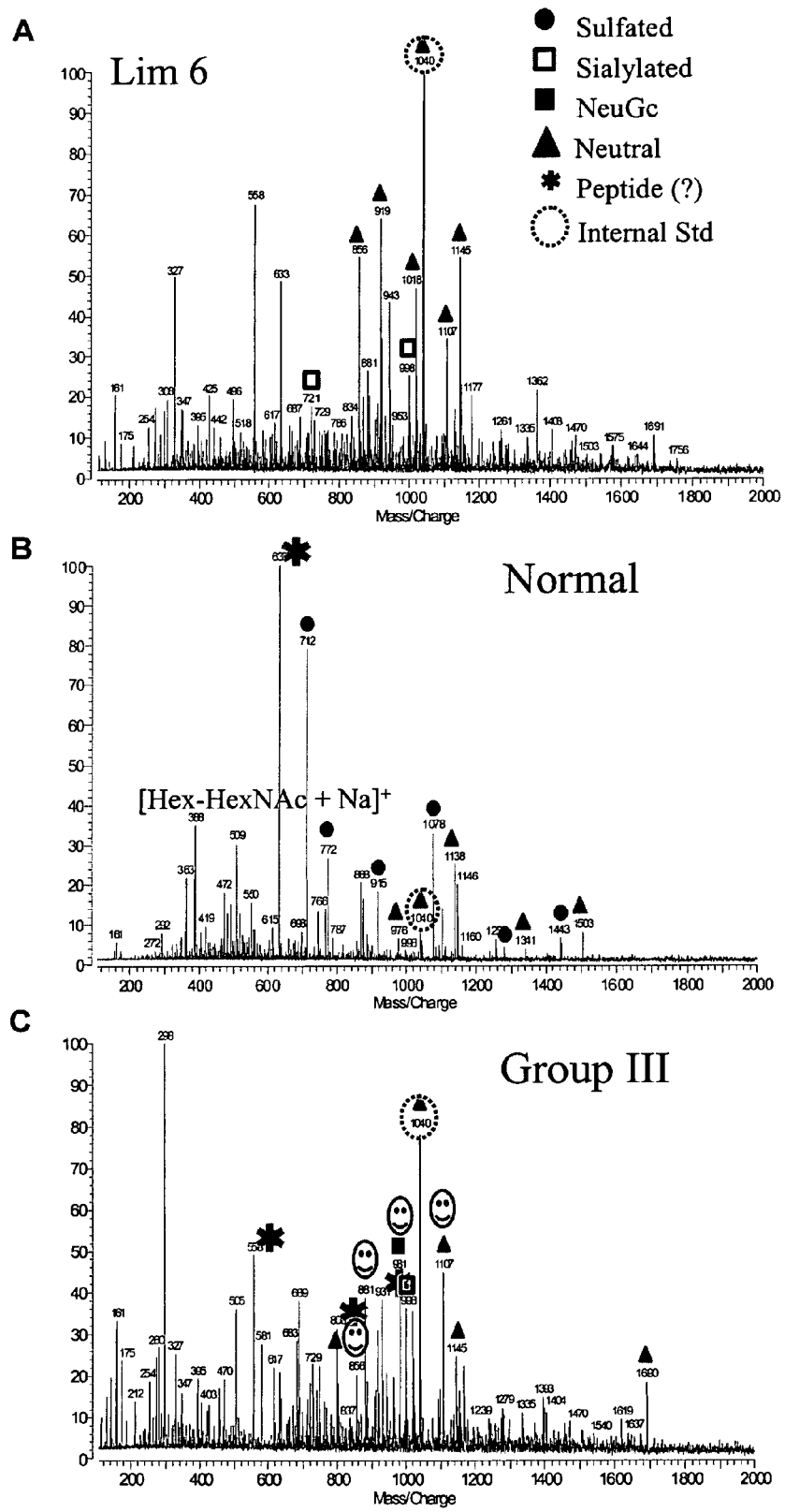
FIG. 13 shows a positive MALDI-FTMS mass spectrum of the O-linked oligosaccharides from a normal sample (A), a Group III sample (B), and a Lim 6 sample (C) eluted by 20% acetonitrile.

FIG. 13 shows the mass spectra of the fraction in the positive mode eluted by 20% acetonitrile from the PGC cartridge for O-linked oligosaccharides from a normal sample (A), a Group III sample (B), and a Lim 6 sample (C). The O-linked oligosaccharides were released by the $NaBH_4$/NaOH treatment and can be classified as neutral, sialylated (NeuAc), NeuGc, or sulfated oligosaccharides. An internal standard (m/z 1040) was included in the analysis of each sample.

FIG. 14 shows the percentage of each class of O-linked oligosaccharide identified in normal (A), Group I (B), Group II (C), Group III (D), and Lim 6 (E) serum samples. A comparison of FIG. 14A with FIG. 14B reveals that the ratio of NeuGc-containing oligosaccharides to NeuAc-containing oligosaccharides has increased in the Group I sample. However, the percentage of sulfated oligosaccharides has decreased in the Group I sample. Group I samples are obtained from individuals with low CA 125 levels, indicating an early stage ovarian cancer. A comparison of FIG. 14A with FIGS. 14C and 14D also reveals a similar increase in the NeuGc/NeuAc oligosaccharide ratio and decrease in the percentage of sulfated oligosaccharides in the Group II and Group III samples. Group II and Group III samples are obtained from individuals with high CA 125 levels, indicating a late stage ovarian cancer. In addition, a comparison of FIG. 14A with FIG. 14E reveals a similar increase in the NeuGc/NeuAc oligosaccharide ratio and decrease in the percentage of sulfated oligosaccharides in the Lim 6 sample. Lim 6 samples are obtained from individuals with extremely high CA 125 levels.

Example 9

Identification of Oligosaccharide Markers Specific to Ovarian Cancer

This example illustrates the identification of oligosaccharide markers that are specific to individuals with low CA 125 levels (Group I), high CA 125 levels (Groups II and III), or extremely high CA 125 levels (Lim 6).

Figure 15:
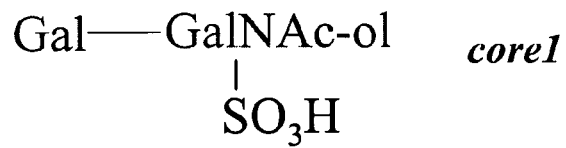
FIG. 15 shows the rudimentary structures of four sulfated O-linked oligosaccharide cancer markers.
Figure 15:
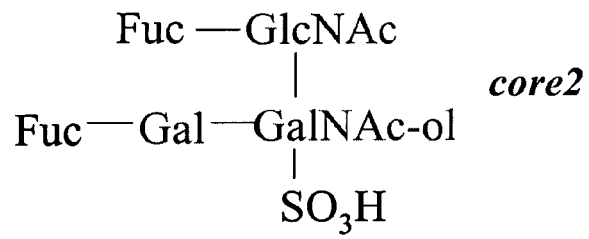
Figure 15:
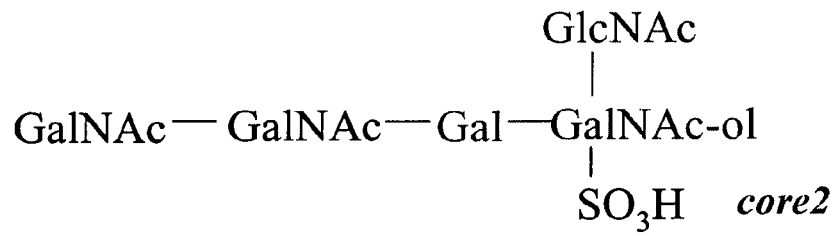
Figure 15:
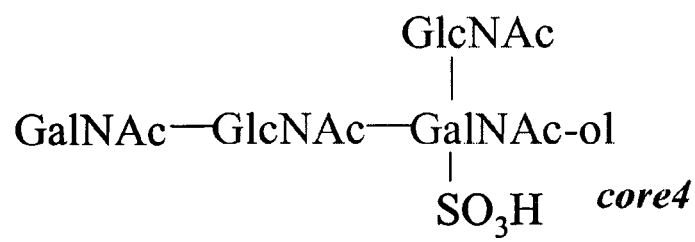

Table 5 shows the m/z ratios of the sulfated O-linked oligosaccharide markers specific to Group I, Group II/III, and Lim 6. Such markers were not found in normal individuals. For example, the presence of sulfated oligosaccharide markers with m/z ratios of 981, 1006, 1038, 1119, and 1468 and the absence of sulfated oligosaccharide markers with m/z ratios of 510 and 1168 are indicative of a Group I sample, i.e., low CA 125 levels with an early stage ovarian cancer. However, the presence of all of the above-mentioned sulfated oligosaccharide markers is indicative of a Group II/III sample, i.e., high CA 125 levels with a late stage ovarian cancer. The presence of only the sulfated oligosaccharide marker with an m/z ratio of 1006 is indicative of a Lim 6 sample, i.e., extremely high CA 125 levels. Table 6 shows the oligosaccharide composition, molecular weight, and observed masses for each of the sulfated oligosaccharide markers described in Table 5. FIG. 15 shows the rudimentary structures, determined using tandem MS, of four of these sulfated oligosaccharide markers. As such, the pattern of sulfated O-linked oligosaccharide markers can be used to determine CA 125 levels and the stage of ovarian cancer in an individual.

TABLE 5

Sulfated O-linked oligosaccharide markers specific to ovarian cancer.

| Sample | CA 125 levels | m/z 510 | m/z 981 | m/z 1006 | m/z 1038 | m/z 1119 | m/z 1168 | m/z 1469 |
|---|---|---|---|---|---|---|---|---|
| Group I | <10 |  | + | + | + | + |  | + |
| Group II | <600 | + | + | + | + | + | + | + |
| Group III | <1100 | + | + | + | + | + | + | + |
| Lim 6 | 11000 |  |  | + |  |  |  |  |
| Normal (A) |  | − | − | − | − | − | − | − |
| Normal (B) |  | − | − | − | − | − | − | − |

"+" indicates the presence of the marker.
"−" indicates the absence of the marker.
"Normal (A)" represents a group of four women without ovarian cancer.
"Normal (B)" represents a male.

TABLE 6

Compositions of the sulfated O-linked oligosaccharide markers specific to ovarian cancer.

| m/z | Oligosaccharide Composition | | | | Molecular Weight | Observed Mass | |
|---|---|---|---|---|---|---|---|
|  | HexNAc | Hex | Fuc | $SO_3H$ | Alditol | $[M + Na]+$ | $[M − H + 2Na]+$ |
| 510 | 1 | 1 |  | 1 | 465.115 | 488.105 | 510.087 |
| 981 | 1 | 3 | 1 | 1 | 935.279 | 958.268 | 980.250 |
| 1006 | 2 | 1 | 2 | 1 | 960.310 | 983.300 | 1005.282 |
| 1038 | 2 | 3 |  | 1 | 992.300 | 1015.290 | 1037.272 |
| 1119 | 4 | 1 |  | 1 | 1074.353 | 1097.343 | 1119.325 |
| 1168 | 2 | 2 | 2 | 1 | 1122.363 | 1145.353 | 1167.335 |
| 1469 | 5 | 1 | 1 | 1 | 1423.491 | 1446.480 | 1468.462 |

Figure 16:
FIG. 16 shows the rudimentary structures of four NeuAc-containing O-linked oligosaccharide cancer markers.
Figure 16:
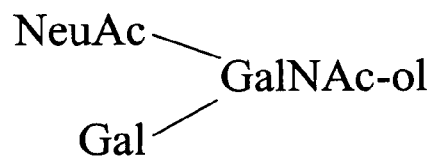
Figure 16:
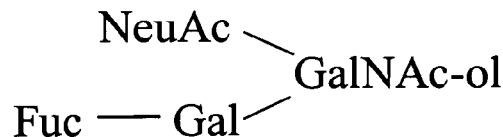
Figure 16:
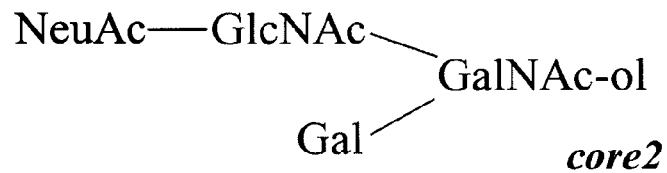

Table 7 shows the m/z ratios of the NeuAc-containing O-linked oligosaccharide markers specific to Group I, Group II/III, and Lim 6. Such markers were not found in normal individuals. For example, the presence of NeuAc-containing oligosaccharide markers with m/z ratios of 721, 908, and 1045 and the absence of NeuAc-containing oligosaccharide markers with m/z ratios of 883, 925, and 1566 are indicative of a Group I sample, i.e., low CA 125 levels with an early stage ovarian cancer. However, the presence of all of the above-mentioned NeuAc-containing oligosaccharide markers is indicative of a Group II/III sample, i.e., high CA 125 levels with a late stage ovarian cancer. The presence of only the NeuAc-containing oligosaccharide markers with m/z ratios of 721 and 1045 is indicative of a Lim 6 sample, i.e., extremely high CA 125 levels. Table 8 shows the oligosaccharide composition, molecular weight, and observed masses for each of the NeuAc-containing oligosaccharide markers described in Table 7. FIG. 16 shows the rudimentary structures, determined using tandem MS, of four of these NeuAc-containing oligosaccharide markers. As such, the pattern of NeuAc-containing O-linked oligosaccharide markers can be used to determine CA 125 levels and the stage of ovarian cancer in an individual.

Figure 17:
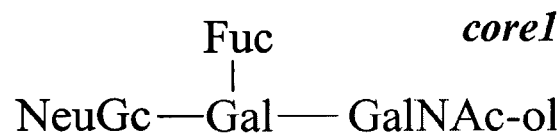
FIG. 17 shows the rudimentary structures of four NeuGc-containing O-linked oligosaccharide cancer markers.
Figure 17:
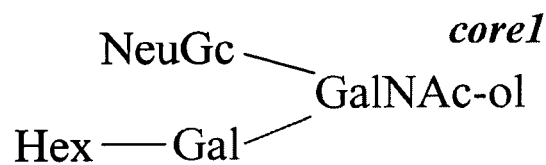
Figure 17:
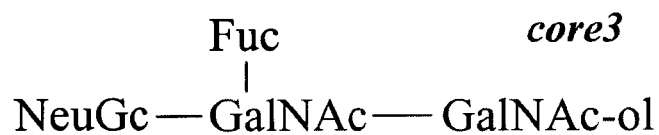
Figure 17:
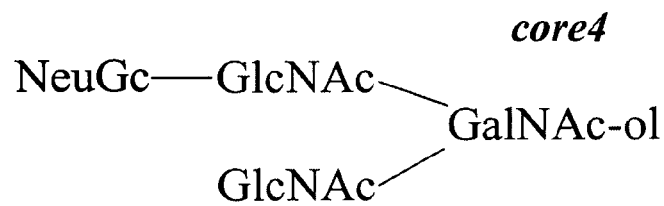

Table 9 shows the m/z ratios of the NeuGc-containing O-linked oligosaccharide markers specific to Group I, Group II/III, and Lim 6. Such markers were not found in normal individuals. For example, the presence of NeuGc-containing oligosaccharide markers with m/z ratios of 899, 981, and 1045 and the absence of NeuGc-containing oligosaccharide markers with m/z ratios of 883, 925, and 1628 are indicative of a Group I sample, i.e., low CA 125 levels with an early stage ovarian cancer. However, the presence of all of the above-mentioned NeuGc-containing oligosaccharide markers is indicative of a Group II/III sample, i.e., high CA 125 levels with a late stage ovarian cancer. The presence of only the NeuGc-containing oligosaccharide markers with m/z ratios of 899 and 1045 is indicative of a Lim 6 sample, i.e., extremely high CA 125 levels. Table 10 shows the oligosaccharide composition, molecular weight, and observed masses for each of the NeuGc-containing oligosaccharide markers described in Table 9. FIG. 17 shows the rudimentary structures, determined using tandem MS, of four of these NeuGc-containing oligosaccharide markers. As such, the pattern of NeuGc-containing O-linked oligosaccharide markers can be used to determine CA 125 levels and the stage of ovarian cancer in an individual.

TABLE 7

NeuAc-containing O-linked oligosaccharide markers specific to ovarian cancer.

| Sample | CA 125 levels | m/z 721 | m/z 883 | m/z 908 | m/z 925 | m/z 1045 | m/z 1566 |
|---|---|---|---|---|---|---|---|
| Group I | <10 | + | | + | | + | |
| Group II | <600 | + | + | + | + | + | + |
| Group III | <1100 | + | + | + | + | + | + |
| Lim 6 | 11000 | + | | | | + | |
| Normal (A) | | − | − | − | − | − | − |
| Normal (B) | | − | − | − | − | − | − |

"+" indicates the presence of the marker.
"−" indicates the absence of the marker.
"Normal (A)" represents a group of four women without ovarian cancer.
"Normal (B)" represents a male.

TABLE 9

NeuGc-containing O-linked oligosaccharide markers specific to ovarian cancer.

| Sample | CA 125 levels | m/z 883 | m/z 899 | m/z 925 | m/z 981 | m/z 1045 | m/z 1628 |
|---|---|---|---|---|---|---|---|
| Group I | <10 | | + | | + | + | |
| Group II | <600 | + | + | + | + | + | + |
| Group III | <1100 | + | + | + | + | + | + |
| Lim 6 | 11000 | | + | | | + | |
| Normal (A) | | − | − | − | − | − | − |
| Normal (B) | | − | − | − | − | − | − |

"+" indicates the presence of the marker.
"−" indicates the absence of the marker.
"Normal (A)" represents a group of four women without ovarian cancer.
"Normal (B)" represents a male.

TABLE 8

Compositions of the NeuAc-containing O-linked oligosaccharide markers specific to ovarian cancer.

| m/z | Oligosaccharide Composition | | | | Molecular Weight | Observed Mass | |
|---|---|---|---|---|---|---|---|
| | HexNAc | Hex | NeuAc | Fuc | Alditol | [M + Na]+ | [M − H + 2Na]+ |
| 721 | 1 | 1 | 1 | | 676.254 | 699.243 | 721.225 |
| 883 | 1 | 2 | 1 | | 838.307 | 861.296 | 883.278 |
| 908 | 2 | | 1 | 1 | 863.338 | 886.328 | 908.310 |
| 925 | 2 | 1 | 1 | | 879.333 | 902.323 | 924.305 |
| 1045 | 1 | 3 | 1 | | 1000.359 | 1023.349 | 1045.331 |
| 1566 | 3 | 1 | 1 | 3 | 1520.586 | 1543.576 | 1565.558 |

TABLE 10

Compositions of the NeuGc-containing O-linked oligosaccharide markers specific to ovarian cancer.

| m/z | Oligosaccharide Composition | | | | Molecular Weight | Observed Mass | |
|---|---|---|---|---|---|---|---|
| | HexNAc | Hex | NeuGc | Fuc | Alditol | [M + Na]+ | [M − H + 2Na]+ |
| 883 | 1 | 1 | 1 | 1 | 838.307 | 861.296 | 883.278 |
| 899 | 1 | 2 | 1 | | 854.301 | 877.291 | 899.273 |
| 925 | 2 | | 1 | 1 | 879.333 | 902.323 | 924.305 |
| 981 | 3 | | 1 | | 936.355 | 959.344 | 981.326 |
| 1045 | 1 | 2 | 1 | 1 | 1000.359 | 1023.349 | 1045.331 |
| 1628 | 3 | 4 | 1 | | 1584.566 | 1607.556 | 1629.537 |

Figure 18:
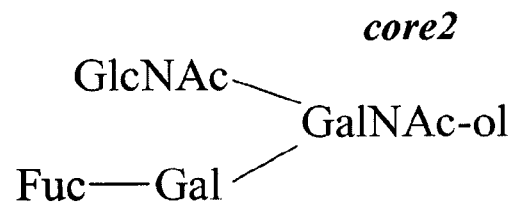
FIG. 18 shows the rudimentary structures of three neutral O-linked oligosaccharide cancer markers.
Figure 18:
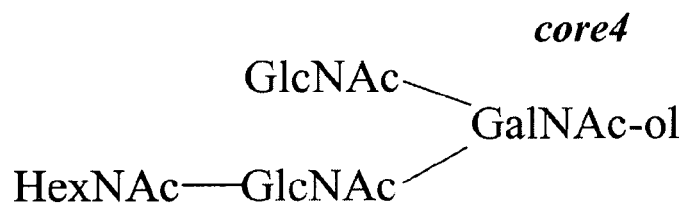
Figure 18:
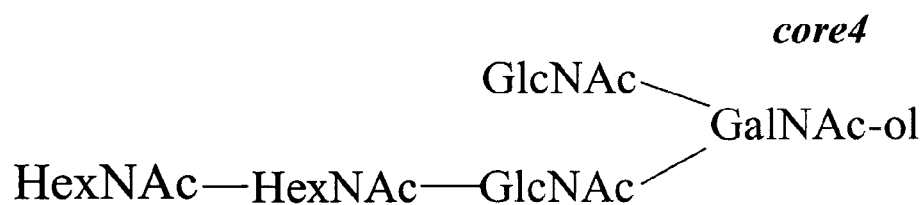

Table 11 shows the m/z ratios of the neutral O-linked oligosaccharide markers specific to Group I, Group II/III, and Lim 6. Such markers were not found in normal individuals. For example, the presence of neutral oligosaccharide markers with m/z ratios of 741, 756, 855, 1018, 1024, 1040, 1107, and 1243 and the absence of neutral oligosaccharide markers with m/z ratios of 538, 862, 1262, 1431, and 1487 are indicative of a Group I sample, i.e., low CA 125 levels with an early stage ovarian cancer. However, the presence of all of the above-mentioned neutral oligosaccharide markers is indicative of a Group II/III sample, i.e., high CA 125 levels with a late stage ovarian cancer. The presence of only the neutral oligosaccharide markers with m/z ratios of 855, 1040, and 1107 is indicative of a Lim 6 sample, i.e., extremely high CA 125 levels. Table 12 shows the oligosaccharide composition, molecular weight, and observed masses for each of the neutral oligosaccharide markers described in Table 11. FIG. 18 shows the rudimentary structures, determined using tandem MS, of three of these neutral oligosaccharide markers. As such, the pattern of neutral O-linked oligosaccharide markers can be used to determine CA 125 levels and the stage of ovarian cancer in an individual.

TABLE 12

Compositions of the neutral O-linked oligosaccharide markers specific to ovarian cancer.

| m/z | Oligosaccharide Composition | | | Molecular Weight | Observed Mass |
|---|---|---|---|---|---|
| | HexNAc | Hex | Fuc | Alditol | [M + Na]+ |
| 538 | 1 | | 2 | 515.221 | 538.211 |
| 741 | 2 | | 2 | 718.301 | 741.290 |
| 756 | 2 | 1 | 1 | 734.296 | 757.285 |
| 855 | 4 | | | 832.344 | 855.333 |
| 862 | 1 | 2 | 2 | 839.327 | 862.317 |
| 1018 | 4 | 1 | | 994.397 | 1017.386 |
| 1024 | 1 | 3 | 2 | 1001.380 | 1024.369 |
| 1040 | 1 | 4 | 1 | 1017.375 | 1040.364 |
| 1107 | 3 | 1 | 2 | 1083.433 | 1106.423 |
| 1243 | 2 | 4 | 1 | 1220.454 | 1243.444 |
| 1262 | 6 | | | 1238.503 | 1261.492 |
| 1431 | 3 | 3 | 2 | 1407.539 | 1430.528 |
| 1487 | 4 | 3 | 1 | 1464.560 | 1487.550 |

TABLE 11

Neutral O-linked oligosaccharide markers specific to ovarian cancer.

| Sample | CA 125 levels | m/z 538 | m/z 741 | m/z 756 | m/z 855 | m/z 862 | m/z 1018 | m/z 1024 | m/z 1040 | m/z 1107 | m/z 1243 | m/z 1262 | m/z 1431 | m/z 1487 |
|---|---|---|---|---|---|---|---|---|---|---|---|---|---|---|
| Group I | <10 | | + | + | + | | + | + | + | + | + | | | |
| Group II | <600 | + | + | + | + | + | + | + | + | + | + | + | + | + |
| Group III | <1100 | + | + | + | + | + | + | + | + | + | + | + | + | + |
| Lim 6 | 11000 | | | | + | | | | + | + | | | | |
| Normal (A) | | − | − | − | − | − | − | − | − | − | − | − | − | − |
| Normal (B) | | − | − | − | − | − | − | − | − | − | − | − | − | − |

"+" indicates the presence of the marker.
"−" indicates the absence of the marker.
"Normal (A)" represents a group of four women without ovarian cancer.
"Normal (B)" represents a male.

Example 10

Identification of Additional Ovarian Cancer Oligosaccharide Markers

This example illustrates the identification of additional oligosaccharide markers that are specific to individuals with ovarian cancer.

Figure 19:
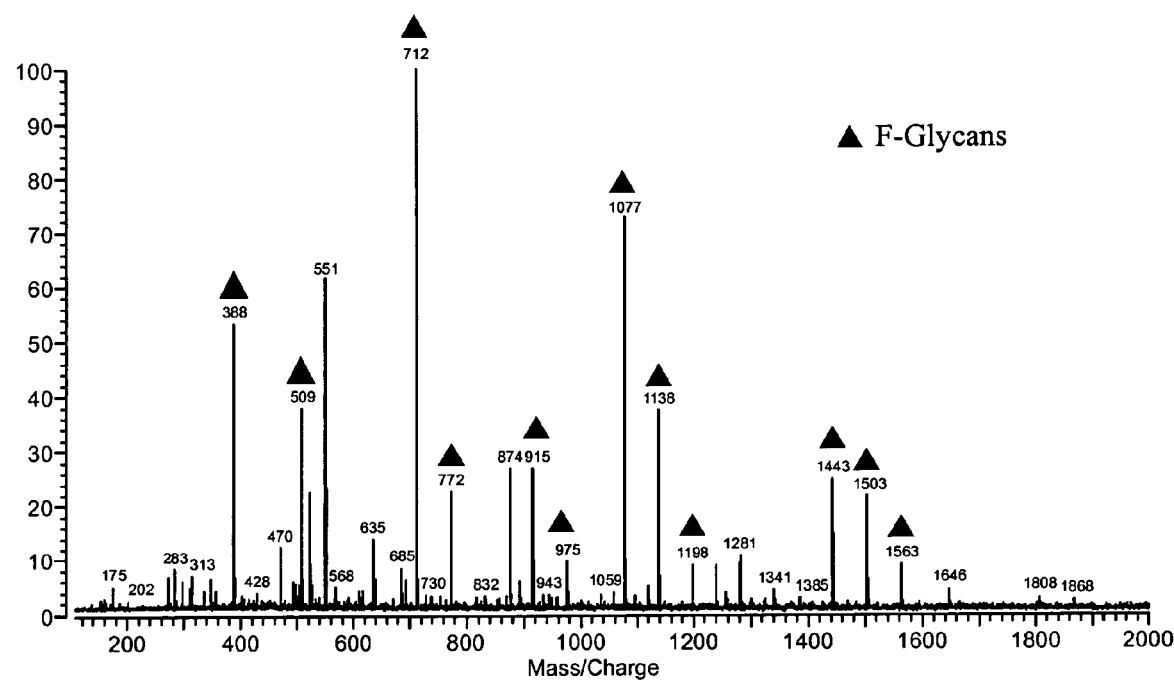
FIG. 19 shows the mass spectrum of the oligosaccharide markers listed in Table 13.

MALDI-FTMS mass spectra were obtained for oligosaccharides from human serum according to the methods of the present invention. Table 13 shows the observed mass (m/z) and oligosaccharide composition of hexose (Hex)-containing O-linked oligosaccharide markers that were identified. FIG. 19 shows the mass spectrum of these oligosaccharides, which are coordinated to Na$^+$.

TABLE 13

Compositions of the Hex-containing O-linked oligosaccharide markers specific to ovarian cancer.

| Observed Mass | Oligosaccharide Composition |
|---|---|
| 347.10 | 2 Hex |
| 388.14 | 1 HexNAc: 1 Hex |
| 509.17 | 3 Hex |
| 550.21 | 1 HexNAc: 2 Hex |
| 712.28 | 3 Hex: 1 HexNAc |
| 772.31 | 1 Hex*: 2 Hex: 1 HexNAc |
| 874.36 | 4 Hex: 1 HexNAc |
| 915.38 | 3 Hex: 2 HexNAc |
| 975.43 | 1 Hex*: 2 Hex: 2 HexNAc |
| 1077.47 | 4 Hex: 2 HexNAc |
| 1137.51 | 1 Hex*: 3 Hex: 2 HexNAc |
| 1239.57 | 5 Hex: 2 HexNAc |
| 1280.62 | 4 Hex: 3 HexNAc |
| 1442.72 | 5 Hex: 3 HexNAc |
| 1502.74 | 1 Hex*: 4 Hex: 3 HexNAc |
| 1562.78 | 2 Hex*: 3 Hex: 1 HexNAc |

All observed ions correspond to $[M-H_2O+Na]^+$.
"Hex" = hexose;
"HexNAc" = N-acetylhexosamine;
"Hex*" = acetyl hexose (i.e., hexose modified with an acetyl group).

Figure 20:
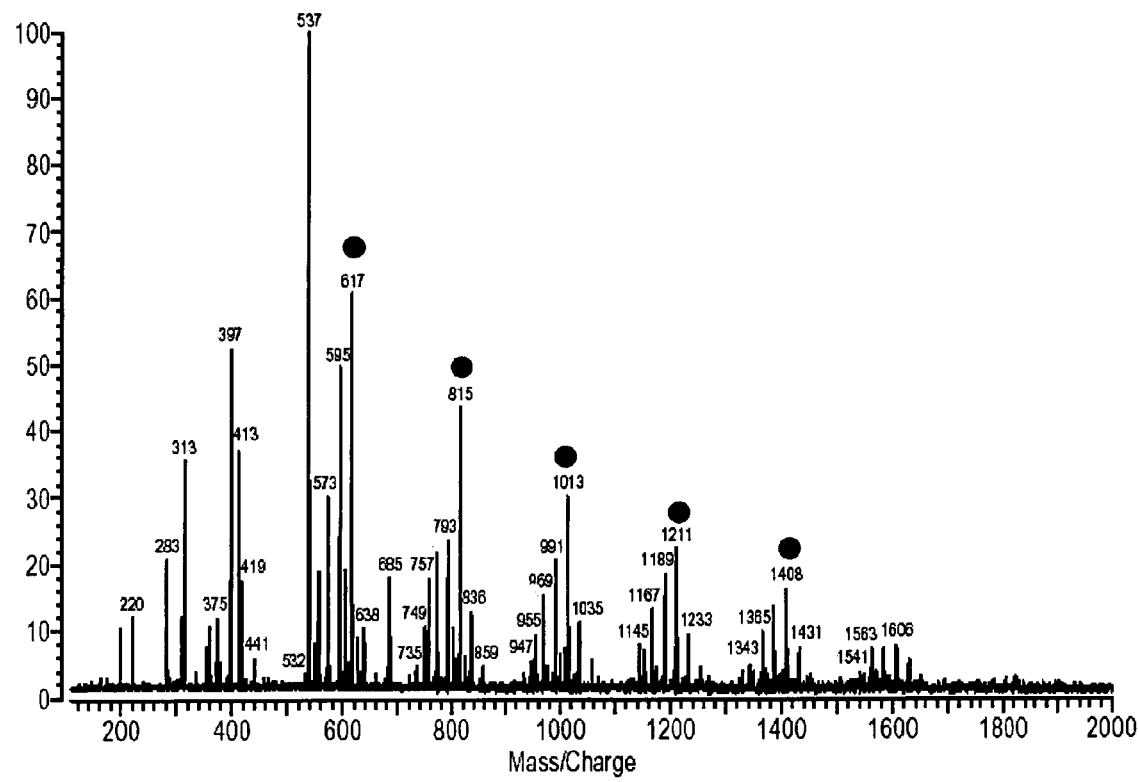
FIG. 20 shows the mass spectrum of the oligosaccharide markers listed in Table 14.

Table 14 shows the observed mass (m/z) and oligosaccharide composition of hexuronic acid (HexA)-containing O-linked oligosaccharide markers that were identified. FIG. 20 shows the mass spectrum of these oligosaccharides, in which the series labeled with solid circles correspond to m/z 616.9696, 814.9582, 1012.9677, 1210.9767, and 1408.9649 in Table 14. These oligosaccharides are coordinated to Na$^+$. However, one skilled in the art will appreciate that the hydrogen atoms in hexuronic acid can be replaced with sodium to yield satellite peaks that are 22 mass units apart.

TABLE 14

Compositions of the HexA-containing O-linked oligosaccharide markers specific to ovarian cancer.

| Series # | Observed Mass | Oligosaccharide Composition |
|---|---|---|
| 1 | 220.9802 | |
|   | 418.9732 | 221 + [HexA]$_1$ |
|   | 616.9696 | 221 + [HexA]$_2$ |
|   | 814.9582 | 221 + [HexA]$_3$ |
|   | 1012.9677 | 221 + [HexA]$_4$ |
|   | 1210.9767 | 221 + [HexA]$_5$ |
|   | 1408.9649 | 221 + [HexA]$_6$ |
|   | 1606.9726 | 221 + [HexA]$_7$ |
| 2 | 361.0110 | |
|   | 559.0082 | 361 + [HexA]$_1$ |
|   | 757.0057 | 361 + [HexA]$_2$ |
|   | 955.0044 | 361 + [HexA]$_3$ |
|   | 1153.0000 | 361 + [HexA]$_4$ |
|   | 1350.9994 | 361 + [HexA]$_5$ |
|   | 1549.0093 | 361 + [HexA]$_6$ |
| 3 | 550.9984 | |
|   | 749.0247 | 551 + [HexA]$_1$ |
|   | 947.0184 | 551 + [HexA]$_2$ |
|   | 1145.0398 | 551 + [HexA]$_3$ |
|   | 1343.0223 | 551 + [HexA]$_4$ |
|   | 1541.0161 | 551 + [HexA]$_5$ |
| 4 | 554.9933 | |
|   | 752.9876 | 555 + [HexA]$_1$ |
|   | 951.0018 | 555 + [HexA]$_2$ |
|   | 1148.9999 | 555 + [HexA]$_3$ |
| 5 | 603.9361 | |
|   | 801.9300 | 604 + [HexA]$_1$ |
|   | 999.9263 | 604 + [HexA]$_2$ |
|   | 1197.9113 | 604 + [HexA]$_3$ |
|   | 1395.9225 | 604 + [HexA]$_4$ |

The mass difference between adjacent peaks is equivalent to exactly one hexuronic acid (HexA) group with one sodium.($\Delta m = 198$).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining a stage, type, or strain of cancer in an individual, said method comprising:
    (a) obtaining a mass spectrum of oligosaccharides from a plurality of glycoproteins in a serum sample from said individual using MALDI-FTMS, wherein the oligosaccharides have been selectively released from said plurality of glycoproteins; and
    (b) comparing the mass spectrum of said oligosaccharides to a mass spectrum profile of oligosaccharides from at least one known stage, type, or strain of cancer,
    wherein said stage, type, or strain of cancer is determined by a similarity between the mass spectrum of said oligosaccharides and the mass spectrum profile of oligosaccharides from said at least one known stage, type, or strain of cancer.

2. The method of 1, wherein said strain of cancer is a strain of ovarian cancer or breast cancer.

3. The method of claim 1, wherein said type of cancer is a type of adenocarcinoma.

4. The method of claim 3, wherein said adenocarcinoma is ovarian cancer or breast cancer.

5. The method of claim 1, wherein said stage of cancer is a stage of ovarian cancer or breast cancer.

6. The method of claim 1, wherein the oligosaccharides are selected from the group consisting of O-linked oligosaccharides, N-linked oligosaccharides, free oligosaccharides, and combinations thereof.

7. A method for diagnosing cancer in an individual, said method comprising:
    (a) obtaining a mass spectrum of oligosaceharides from a plurality of glycoproteins in a serum sample from said individual using MALDI-FTMS, wherein the oligosaceharides have been selectively released from said plurality of glycoproteins; and
    (b) comparing the mass spectrum of said oligosaccharides to a mass spectrum profile of oligosaccharides from a control sample, wherein said control sample is a sample from a normal cell line or an individual not having cancer, and wherein a higher ratio of NeuGc-containing O-linked oligosaccharides to NeuAc-containing O-linked oligosaccharides in the mass spectrum of said oligosaccharides relative to the mass spectrum profile of oligosaccharides from said control sample indicates that said individual has cancer.

8. The method of claim 7, wherein said cancer is an adenocarcinoma.

9. The method of claim 8, wherein said adenocarcinoma is ovarian cancer or breast cancer.

10. A method for diagnosing cancer in an individual, said method comprising:
   (a) obtaining a mass spectrum of oligosaccharides from a plurality of glycoproteins in a serum sample from said individual, wherein the oligosaccharides have been selectively released from said plurality of glycoproteins; and
   (b) determining the presence or absence of a cancer marker selected from the group consisting of a sulfated oligosaccharide, an N-acetylneuraminic acid (NeuAc)-containing oligosaccharide, an N-glycolylneuraminic acid (NeuGc)-containing oligosaccharide, a neutral oligosaccharide, a hexose (Hex)-containing oligosaccharide, a hexuronic acid (HexA)-containing oligosaccharide, and combinations thereof in the mass spectrum of said oligosaccharides,
   wherein the presence of said cancer marker indicates that said individual has cancer.

11. The method of claim 10, wherein said cancer is an adenocarcinoma.

12. The method of claim 11, wherein said adenocarcinoma is ovarian cancer or breast cancer.

13. The method of claim 10, wherein said Hex-containing oligosaccharide has a composition selected from the group consisting of 2 Hex; 1 HexNAc:1 Hex; 3 Hex; 1 HexNAc:2 Hex; 3 Hex:1 HexNAc; 1 Hex*:2 Hex:1 HexNAc; 4 Hex:1 HexNAc; 3 Hex:2 HexNAc; 1 Hex*:2 Hex:2 HexNAc; 4 Hex:2 HexNAc; 1 Hex*:3 Hex:2 HexNAc; 5 Hex:2 HexNAc; 4 Hex:3 HexNAc; 5 Hex:3 HexNAc; 1 Hex*:4 Hex:3 HexNAc; 2 Hex*:3 Hex:1 HexNAc; and combinations thereof.

14. The method of claim 10, wherein said HexA-containing oligosaccharide has a composition selected from the group consisting of m/z 221+[HexA]$_1$; m/z 221+[HexA]$_2$; m/z 221+[HexA]$_3$; m/z 221+[HexA]$_4$; m/z 221+[HexA]$_5$; m/z 221+[HexA]$_6$; m/z 221+[HexA]$_7$; m/z 361+[HexA]$_1$; m/z 361+[HexA]$_2$; m/z 361+[HexA]$_3$; m/z 361+[HexA]$_4$; m/z 361+[HexA]$_5$; m/z 361+[HexA]$_6$; m/z 551+[HexA]$_1$; m/z 551+[HexA]$_2$; m/z 551+[HexA]$_3$; m/z 551+[HexA]$_4$; m/z 551+[HexA]$_5$; m/z 555+[HexA]$_1$; m/z 555+[HexA]$_2$; m/z 555+[HexA]$_3$; m/z 604+[HexA]$_1$; m/z 604+[HexA]$_2$; m/z 604+[HexA]$_3$; m/z 604+[HexA]$_4$; and combinations thereof.

15. The method of claim 10, wherein the oligosaccharides are selected from the group consisting of O-linked oligosaccharides, N-linked oligosaccharides, free oligosaccharides, and combinations thereof.

16. A method for diagnosing a stage of cancer in an individual, said method comprising:
   (a) obtaining a mass spectrum of oligosaccharides from a plurality of glycoproteins in a serum sample from said individual, wherein the oligosaccharides have been selectively released from said plurality of glycoproteins;
   (b) determining the presence or absence of a first cancer marker in the mass spectrum of said oligosaccharides, wherein said first cancer marker is selected from the group consisting of 1 HexNAc:1 Hex:1 NeuAc; 2 HexNAc:1 NeuAc:1 Fuc; 1 HexNAc:3 Hex:1 NeuAc; 1 HexNAc:2 Hex:1 NeuGc; 3 HexNAc:1 NeuGe; 1 HexNAc:2 Hex:1 NeuGc:1 Fuc; 1 HexNAc:3 Hex:1Fuc:1 SO$_3$H; 2 HexNAc:1 Hex:2 Fuc:1 SO$_3$H; 2 HexNAc:3 Hex:1 SO$_3$H; 4 HexNAc:1 Hex:1 SO$_3$H; 5 HexNAc:1 Hex:1 Fuc:1 SO$_3$H; 2 HexNAc:2 Fuc; 2 HexNAc:1 Hex:1 Fuc; 4 HexNAc; 4 HexNAc:1 Hex; 1 HexNAc:3 Hex:2 Fuc; 1 HexNAc:4 Hex:1 Fuc; 3 HexNAc: 1 Hex:2 Fuc; 2 HexNAc:4 Hex: 1 Fuc; and combinations thereof; and
   (c) determining the presence or absence of a second cancer marker in the mass spectrum of said oligosaccharides, wherein said second cancer marker is selected from the group consisting of 1 HexNAc:2 Hex:1 NeuAc; 2 HexNAc:1 Hex:1 NeuAc; 3 HexNAc:1 Hex:1 NeuAc:3 Fuc; 1 HexNAc:1 Hex:1 NeuGc:1 Fuc; 2 HexNAc:1 NeuGc:1 Fuc; 3 HexNAc:4 Hex:1 NeuGc; 1 HexNAc:1 Hex:1 SO$_3$H; 2 HexNAc:2 Hex:2 Fuc:1 SO$_3$H; 1 HexNAc:2 Fuc; 1 HexNAc:2 Hex:2 Fuc; 6 HexNAc; 3 HexNAc:3 Hex:2 Fuc; 4 HexNAc:3 Hex:1 Fuc; and combinations thereof,
   wherein the presence of said first cancer marker and the absence of said second cancer marker indicates that said individual has an early, stage cancer and wherein the presence of said second cancer marker indicates that said individual has a late stage cancer.

17. The method of claim 16, wherein said early stage cancer is an early stage ovarian cancer.

18. The method of claim 17, wherein said early stage ovarian cancer is associated with low CA 125 levels.

19. The method of claim 16, wherein said late stage cancer is a late stage ovarian cancer.

20. The method of claim 19, wherein said late stage ovarian cancer is associated with high CA 125 levels.

21. The method of claim 16, wherein the oligosaccharides are selected from the group consisting of O-linked oligosaccharides, N-linked oligosaccharides, free oligosaccharides, and combinations thereof.

22. A method for diagnosing cancer in an individual, said method comprising:
   (a) obtaining a mass spectrum of oligosacoharides from a plurality of glycoproteins in a serum sample from said individual using MALDI-FTMS, wherein the oligosaccharides have been selectively released from said plurality of glycoproteins;
   (b) comparing the mass spectrum of said oligosaceharides to a mass spectrum profile of oligosaceharides from a cancer sample; and
   (c) diagnosing cancer by a similarity between the mass spectrum of said oligosaccharides and the mass spectrum profile of oligosaccharides from said cancer sample.

23. The method of claim 22, wherein said cancer is an adenocarcinoma.

24. The method of claim 23, wherein said adenocarcinoma is ovarian cancer or breast cancer.

25. The method of claim 22, wherein said cancer sample is a sample from a cancer cell line or an individual having cancer.

26. The method of claim 22, wherein the oligosaccharides are selected from the group consisting of O-linked oligosaccharides, N-linked oligosaccharides, free oligosaccharides, and combinations thereof.

* * * * *

UNITED STATES PATENT AND TRADEMARK OFFICE
CERTIFICATE OF CORRECTION

PATENT NO. : 7,651,847 B2
APPLICATION NO. : 11/157478
DATED : January 26, 2010
INVENTOR(S) : Carlito B. Lebrilla et al.

It is certified that error appears in the above-identified patent and that said Letters Patent is hereby corrected as shown below:

Claim 7, Column 42, Line 60:

"(a) obtaining a mass spectrum of oligosaceharides from a"

should read:

-- (a) obtaining a mass spectrum of oligosaccharides from a --

Claim 7, Column 42, Line 63 and 64:

"individual using MALDI-FTMS, wherein the oligosaceharides have been selectively released from said plural-"

should read:

-- individual using MALDI-FTMS, wherein the oligosaccharides have been selectively released from said plural- --

Claim 10, Column 43, Lines 24-27:

"acid (NeuGc)-containing oligosaccharide, a neutral oligosaceharide, a hexose (Hex)-containing oligosaceharide, a hexuronic acid (HexA)-containing oligosaceharide, and combinations thereof in the mass spectrum"

should read:

-- acid (NeuGc)-containing oligosaccharide, a neutral oligosaccharide, a hexose (Hex)-containing oligosaccharide, a hexuronic acid (HexA)-containing oligosaccharide, and combinations thereof in the mass spectrum --

Claim 22, Column 44, Line 43:

"(a) obtaining a mass spectrum of oligosacoharides from a"

should read:

-- (a) obtaining a mass spectrum of oligosaccharides from a --

CERTIFICATE OF CORRECTION (continued)
U.S. Pat. No. 7,651,847 B2

Claim 22, Column 44, Line 48:

"(b) comparing the mass spectrum of said oligosaceharides"

should read:

-- (b) comparing the mass spectrum of said oligosaccharides --

Claim 22, Column 44, Line 49:

"to a mass spectrum profile of oligosaceharides from a"

should read:

-- to a mass spectrum profile of oligosaccharides from a --

Signed and Sealed this

Twentieth Day of April, 2010

David J. Kappos
*Director of the United States Patent and Trademark Office*